(12) United States Patent
Ichim

(10) Patent No.: US 9,598,673 B2
(45) Date of Patent: Mar. 21, 2017

(54) TREATMENT OF DISC DEGENERATIVE DISEASE

(75) Inventor: Thomas E. Ichim, San Diego, CA (US)

(73) Assignee: Creative Medical Health, Phoenix, AZ (US)

(*) Notice: Subject to any disclaimer, the term of this patent is extended or adjusted under 35 U.S.C. 154(b) by 680 days.

(21) Appl. No.: 12/301,597

(22) PCT Filed: May 18, 2007

(86) PCT No.: PCT/US2007/011778
§ 371 (c)(1),
(2), (4) Date: Sep. 30, 2009

(87) PCT Pub. No.: WO2007/136673
PCT Pub. Date: Nov. 29, 2007

(65) Prior Publication Data
US 2010/0008992 A1  Jan. 14, 2010

Related U.S. Application Data

(60) Provisional application No. 60/801,957, filed on May 19, 2006.

(51) Int. Cl.
| | | |
|---|---|---|
| *C12N 5/0775* | (2010.01) | |
| *A61K 35/28* | (2015.01) | |
| *C12N 5/078* | (2010.01) | |
| *A61K 38/18* | (2006.01) | |
| *A61K 38/19* | (2006.01) | |
| *A61K 35/17* | (2015.01) | |
| *A61K 35/51* | (2015.01) | |
| *A61K 35/545* | (2015.01) | |

(52) U.S. Cl.
CPC ............ *C12N 5/0634* (2013.01); *A61K 35/17* (2013.01); *A61K 35/28* (2013.01); *A61K 35/51* (2013.01); *A61K 35/545* (2013.01); *A61K 38/18* (2013.01); *A61K 38/193* (2013.01); *C12N 5/0663* (2013.01); *C12N 5/0665* (2013.01); *C12N 2500/36* (2013.01); *C12N 2501/22* (2013.01); *C12N 2501/23* (2013.01)

(58) Field of Classification Search
CPC ..... C12N 5/0663; C12N 5/0665; A61K 35/28
See application file for complete search history.

(56) References Cited

U.S. PATENT DOCUMENTS

| 5,591,625 A | 1/1997 | Gerson et al. | |
| 6,806,251 B2* | 10/2004 | Lamb | 424/780 |
| 2001/0041679 A1* | 11/2001 | Rosengart | A61K 38/1866 514/44 R |
| 2001/0055587 A1* | 12/2001 | Dinsmore et al. | 424/93.7 |
| 2004/0151707 A1* | 8/2004 | Flugelman et al. | 424/93.21 |
| 2004/0210209 A1* | 10/2004 | Yeung et al. | 604/500 |
| 2004/0229786 A1 | 11/2004 | Attawia et al. | |
| 2004/0258670 A1* | 12/2004 | Laughlin et al. | 424/93.21 |
| 2005/0118714 A1* | 6/2005 | Ha et al. | 435/372 |
| 2005/0232903 A1* | 10/2005 | Hanley et al. | 424/93.7 |
| 2005/0239897 A1* | 10/2005 | Pittenger et al. | 514/569 |
| 2006/0292164 A1* | 12/2006 | Horwitz | 424/185.1 |
| 2007/0003525 A1* | 1/2007 | Moehlenbruck et al. | 424/93.7 |

FOREIGN PATENT DOCUMENTS

| WO | WO00/49136 | | 8/2000 |
| WO | WO 01/20999 | * | 3/2001 |
| WO | WO01/20999 | | 3/2001 |
| WO | WO2005/085421 | | 9/2005 |

OTHER PUBLICATIONS

Kauppila, et al. Spine, 2004, 29:2147-2152.*
Maccario et al Haematologica, 2005, 90:516-525.*
Adler, et al. AJR 2005. Am J Roentgenol 185:940-943).*
Kauppila et al Acta Radiol 1994. 35:541-544.*
Sofka et al J Ultrasound Med 20:21-26, 2001).*
Kurunlahti et al. Radiology, 2001, 221, 779-786.*
Kauppila, et al Annals of the Rheumatic Diseases 1997;56:591-595.*
Kauppila et al. Spine , 2004, 29, 2147-2152.*
Dumont et al Neurosurgery, 2002, 51:1239-1245.*
Chernoff (2002, Protein-Protein Interactions: A Molecular Cloning Manual, Cold Spring Laboratory Press, Chapter 2, pp. 7-13.*
Kortesidis et al. (2005, Blood, vol. 105, pp. 3793-3801.*
Gimble et al., 2003, Cytotherapy, vol. 5(5), pp. 362-369.*
Eggenhofer et al. (2014, Frontiers in Immunology, vol. 5(148), pp. 1-6.*
Guillot et al. 2007, J. Cell. Mol. Med., vol. 11(5), pp. 935-944.*
Lakshmipathy et al. (2005, Blood Rev., vol. 19, pp. 29-38.*
Jain et al (Nat Med. 2000; 6(2): 131-132.*
Samstein et al Journal of American Society of Nephrology 12: 182-193, 2001.*
Spangers Kidney International (2008) 74, 14-21.*
Acosta, et al., "The potential role of mesenchymal stem cell therapy for intervertebral disc degeneration: a critical overview" *Neurosurg Focus* (2005) 19(3): 1-6.
Helm, et al., "Future use of mesenchymal stem cells in spine surgery" *Neurosurg Focus* (2005) 19(6): 1-5.
Risbud, et al., "Stem cell regeneration of the nucleus pulposus" *The Spine Journal* (2004) 4: 348S-353S.
Sakai, et al., "Differentiation of Mesenchymal Stem Cells Transplated to a Rabbit Degenerative Disc Model: Potential and Limitations for Stem Cell Therapy in Disc Regeneration" *Spine* (2005) 30(21): 2379-2387.
Sakai, et al., "Regenerative effects of transplanting mesenchymal stem cells embedded in atelocollagen to the degenerated intervertebral disc" *Biomaterials* (2006) 27: 335-345.
Sakai, et al., "Transplantation of mesenchymal stem cells embedded in Atelocollagen® get to the intervertebral disc: a potential therapeutic model for disc degeneration" *Biomaterial* (2003) 24: 3531-3541.
International Search Report and Written Opinion, dated Jan. 21, 2008, issued in International Application No. PCT/US2007/011778.

* cited by examiner

*Primary Examiner* — Anoop Singh
(74) *Attorney, Agent, or Firm* — Baumgartner Patent Law; Marc Baumgartner

(57) ABSTRACT

Methods and compositions for treating or ameliorating lower back pain by administering an effective amount of one or more cell types, alone, and/or in combination with a matrix, and/or in combination with growth factors, in order to stimulate lumbar angiogenesis, decrease inflammation, and stimulating regeneration.

4 Claims, No Drawings

TREATMENT OF DISC DEGENERATIVE DISEASE

CROSS-REFERENCE TO RELATED APPLICATIONS

This application is a U.S. National Phase of International Application No. PCT/US2007/011778, filed May 18, 2007, designating the U.S. and published on Nov. 29, 2007 as WO 2007/136673, which claims priority to U.S. Application No. 60/801,957, filed May 19, 2006. The entire content of these applications is incorporated herein by reference in its entirety.

FIELD OF THE INVENTION

The invention disclosed generally pertains to the field of treating lower back pain. The invention teaches compositions of matter, cellular compositions, and methods for treatment of lower back disorders that cause lower back pain.

BACKGROUND OF THE INVENTION

Anatomy of the Spine

In humans the spine is composed of bony structures called vertebrae, separated by intervertebral discs. One of the main functions of the vertebrae is to provide structural support and protection for the spinal cord. Each vertebrae is comprised of a spinous process, a bony prominence behind the spinal cord, which shields the cord's nervous tissue on the back side, two bony protrusions on the sides called transverse processes, and a "body" in front of the spinal cord which provides a structural support for weight-bearing. The average adult has 24 vertebrae, although at birth 33 are present, this is due to fusion during normal development. The vertebrae are divided by anatomical locations with 7 in the neck, also called the cervical vertebrae, 12 in the middle back, called the thoracic vertebrae, 5 in the lower back, called the lumbar vertebrae, and the sacrum, which is actually formed from five fused vertebrae. The tailbone, called the coccyx is made of three fused vertebrae. Of these, the lumbar vertebrae are the largest, in part since they are responsible for carrying the majority of body weight. Due to this, the lumbar area is associated with the highest level of degeneration and is believed causative for a wide variety of pain-inducing syndromes.

Disc Biology

Separating the vertebrae are soft intervertebral discs that, together with the two facet joints, allow for movement of the vertebrae and therefore provide the ability of the spine to move in various directions. The complex of two facet joints posteriorly and the disc anteriorly is referred to as a spinal segment. The intervertebral disc is composed of the annulus fibrosus, the nucleus pulposus, and the cartilage endplate. The nucleus pulposus is comprised of anionic proteoglycans, such as aggracan, that have high affinity for water, and provide a cushioning and shock-absorbing function. The annulus fibrosis encapsulates the nucleus pulposus, and is composed of concentrically organized layers of collagen fibrils (lamellae). The composition of the nucleus pulposus is distinctly different than the annulus fibrosis since the former consists primarily of a jelly-like substance and high collagen type I, whereas the latter is made of a solid, fibrotic-like texture, primarily containing collagen type II. In the adult the cartilage endplate is composed primarily of hyaline cartilage and serves to separate the nucleus pulposus and annulus fibrosus from the adjacent vertebral bone.

Chronic Back Pain

Musculoskeletal disorders of the spine are an extremely common occurrence associated with debilitating back pain, leading to enormous psychosocial and economic ramifications. Lower-back pain is the leading source of disability in people under 45 years of age, and it results in significant economic losses (Frymoyer J. W. 1997. The economics of spinal disorders. In Frymoyer et al., eds. The adult spine: principles and practice. Philadelphia, Pa.: Lippincott-Raven, 143-50, which is incorporated by reference herein in its entirety). 80% of people in the United States will experience back pain at some point in their lifetime (Lively, M. W. 2002. *South Med J* 95:642-646, which is incorporated by reference herein in its entirety), and it is the second most common reason for symptomatic physician visits (Hart, et al. 1995. *Spine* 20:11-19, which is incorporated by reference herein in its entirety). Causes of back pain range from injury induced, which presents as a minor problem, accelerating to a chronic disorder, as well as degenerative spine diseases that lead to degenerative spondylolisthesis and spinal stenosis. The vast majority of chronic back pain is associated with degeneration of the intervertebral disc, which can manifest in many different clinical conditions including spinal stenosis and instability, radiculopathy, myelopathy, and disc herniation.

Although the association between disc degeneration and chronic back pain has been established, disc degeneration can also occur without back pain. Disc degeneration can occur as a natural process, in many individuals asymptomatically. The origin of pain has therefore been termed "discogenic" not necessarily because of the disc degenerative process, but in part due to the granulation tissue that invades the disc space and causes inflammation and nociception (Peng, et al. 2006. *Spine* 31:560-566, which is incorporated by reference herein in its entirety).

There is a prevalent view that the majority of lower back pain that is associated with disc degeneration is caused by nerve root compression (radiculopathic pain), however, magnetic resonance imaging many times does not detect compression of verves, even in patients which have sciatica (Freemont, et al. 1997. *Lancet* 350:178-181, which is incorporated by reference herein in its entirety). More recent studies suggest that lumbar disc herniation itself is not the major cause of lower back pain, but instead the discogenic pain is caused by anular disruption, such as an annular tear (Schwarzer, et al. 1995. *Spine* 20:1878-1883; Saifuddin, et al. 1998. *Spine* 23:453-457; Ito, et al. 1998. *Spine* 23:1252-1258; discussion 1259-1260; Moneta, et al. 1994. *Spine* 19:1968-1974, each of which is incorporated by reference herein in its entirety). The fact that the annulus itself is surrounded by various nerve endings allows the possibility that inflammation associated with the disruptions of the annular rings is what triggers pain (Peng, et al. 2005. *J Bone Joint Surg Br* 87:62-67, which is incorporated by reference herein in its entirety).

SUMMARY OF THE INVENTION

The present invention relates to methods and compositions for treating or ameliorating lower back pain comprising administering to an animal, preferably a human, an effective amount of one or more cell types, alone, and/or in combination with a matrix, and/or in combination with growth factors, in order to stimulate lumbar angiogenesis, decrease inflammation, and stimulating regeneration. While the concept of therapeutic angiogenesis has been intensively investigated for treatment of heart disease, peripheral arterial disease, and other ischemia-related pathologies, this invention teaches the use of cellular therapy for stimulation of angiogenesis and/or anti-inflammatory activities in the context of lower back pain associated with disc degeneration. The uniqueness of this approach is that in contrast to conventionally used angiogenic stimuli such as growth factors and small molecules, administration of angiogenesis-stimulating cells provides a more physiological means of blood-vessel formation. Additionally, cell types can be chosen to provide not only stimulation of angiogenesis but also upregulation of anti-inflammatory activities. Furthermore, the invention teaches that certain combinations of antigenesis inducing cell types can be administered with anti-inflammatory cells in order to provide additive and/or synergistic therapeutic benefit. While it is known that cells such as CD34+, CD31+ bone marrow derived cells trigger angiogenesis, these cells also secrete a variety of molecules such as TGF-b which suppress inflammation and local immunological activity (Rossner, et al. 2005. *Eur J Immunol* 35:3533-3544; Angulo, et al. 2000. *Eur J Immunol* 30:1263-1271, each of which is incorporated by reference herein in its entirety). Furthermore, other populations of bone marrow cells possess such properties. One specific population is the mesenchymal stem cell. Anti-inflammatory cells found in the bone marrow such as natural killer T cells and CD4+ CD25+ T regulatory cells (Treg) can also be used within the teachings of the present invention. Accordingly, in one aspect the invention teaches the therapeutic use of such cells, either purified, or as a heterogenous population of bone marrow mononuclear cells. In another aspect, cells with anti-inflammatory and/or angiogenesis stimulating ability can be isolated from sources such as placenta, cord blood, and adipose tissue. Said cells can be autologous, allogeneic, or xenogeneic. Said cells can be capable of endogenously stimulating angiogenesis, or can be induced to stimulate angiogenesis. Furthermore, said cells can possess an anti-inflammatory activity or activities which suppresses cascades involved in the disc degeneration and atherosclerotic processes. In some aspects of the invention endowment or upregulation of angiogenesis stimulation ability can be accomplished by transfection of angiogenesis promoting genes, exposure to specific culture conditions, or co-culture with other cell types. Examples of angiogenesis stimulating genes include but are not limited to VEGF, FGF-1, FGF-2, FGF-4, EGF, HGF, HIF-1a, HIF-2, NET, and NF-kB.

In one aspect of this invention, methods of treating disc degeneration are disclosed through the intramuscular administration of cells capable of stimulating production of new blood vessels. Said cells include stem cells of a variety of subtypes such as side population, embryonic, germinal, endothelial, hematopoietic, myoblast, placental, cord-blood, adipocyte and mesenchymal stem cells.

In another aspect of the invention, cell compositions useful for the treatment or amelioration of lower back pain are provided. Said cells naturally express at least one growth factor capable of stimulating angiogenesis.

In another aspect of the invention, cell compositions useful for the treatment or amelioration of lower back pain are either allogeneic or xenogeneic, but encapsulated in order to inhibit immune mediated rejection.

In another aspect of the invention cells with ability to stimulate angiogenesis are transfected with a receptor to enhance migration towards areas of hypoxia, said receptor can include, for example, CXCR-4, VEGF-R1, VEGF-R2, and CCR1.

In another aspect of the invention, cells capable of stimulating angiogenesis are injected into muscles identified as being ischemic in patients with lumbar pain. Said muscles could include the psoas major muscle, the multifidus muscle, the transversospinalis muscle and the sacrospinalis muscle.

Another aspect of the invention provides an off-the-shelf cellular therapy comprising a bank of mesenchymal stem cells stored to substantially match the human population at various HLA loci. Said cells are cryopreserved until patients present with lower back pain and meet certain inclusion and exclusion criteria suggesting they would benefit from implantation of said cells. Said patients are treated by administration of said cells into an area proximal to the circulation of the lumbar segment causative of pain. Said cells are substantially localized and do not undergo rapid immunologically mediated rejection due to inherent immunosuppressive and anti-inflammatory properties. Said cells release angiogenic agents capable of increasing overall perfusion to said patient lumbar segment causative of pain.

Accordingly, provided herein is a method of inhibition and/or reversal of disc degeneration comprising administration of cells capable of augmenting the rate of perfusion to the area of disc degeneration.

Also provided herein is a method of treating disc degenerative disease, comprising administering cells capable of increasing angiogenesis.

Also provided herein is a method of accelerating herniated disc resorption, comprising administering cells capable of increasing angiogenesis.

Also provided herein is a method of treatment of a patient with herniated disc(s) and/or disc degeneration comprising administering a mixture of cells and a matrix.

In certain aspects, the cells can be autologous, allogeneic or xenogeneic. In some aspects, the cells are substantially composed of stem cells and can be selected from the group consisting of side population, embryonic, germinal, endothelial, hematopoietic, myoblast, placental, cord-blood, adipocyte and mesenchymal stem cells. In certain aspects, the side population stem cells are identified based on expression of the multidrug resistance transport protein (ABCG2) or ability to efflux intracellular dyes such as rhodamine-123 and or Hoechst 33342. In certain aspects, the embryonic stem cells are identified based on expression of one or more antigens selected from the group consisting of: stage-specific embryonic antigens (SSEA) 3, SSEA 4, Tra-1-60 and Tra-1-81, Oct-3/4, Cripto, gastrin-releasing peptide (GRP) receptor, podocalyxin-like protein (PODXL), and human telomerase reverse transcriptase (hTERT). In certain aspects, the germinal stem cells are identified based on expression of one or more antigens selected from the group consisting of: SSEA-4, GCTM-2 antigen, TRA 1-60, Cripto, gastrin-releasing peptide (GRP) receptor, podocalyxin-like protein (PODXL), and human telomerase reverse transcriptase (hTERT). In certain aspects, the endothelial stem cells are identified based on expression of one or more antigens selected from the group consisting of: CD31, CD34, AC133, CD146 and flk1. In certain aspects, the hematopoietic stem cells are identified based on expression of one or more antigens selected from the group consisting of: CD34, c-kit, flk-1, and CXCR-4. In certain aspects, the myoblast stem cells are identified based on expression of one or more antigens selected from the group consisting of: Pax7, MyoD, and AC133. In certain aspects, the placental stem cells are identified based on expression of one or more antigens selected from the group consisting of: Oct-4, Rex-1, CD9, CD13, CD29, CD44, CD166, CD90, CD105, SH-3, SH-4, TRA-1-60, TRA-1-81, SSEA-4 and Sox-2. In certain aspects, the cord blood stem cells are identified based on expression of one or more antigens selected from the group consisting of: CD34, c-kit, and CXCR-4. In certain aspects, the adipocyte stem cells are identified based on expression of one or more antigens selected from the group consisting of: CD13, CD29, CD44, CD63, CD73, CD90, CD166, Aldehyde dehydrogenase (ALDH), and ABCG2. In certain aspects, the mesenchymal stem cells are identified based on expression of one or more antigens selected from the group consisting of: STRO-1, CD105, CD54, CD106, HLA-I markers, vimentin, alpha-smooth muscle actin (ASMA), collagen-1, and fibronectin, but not HLA-DR, CD117, and hemopoietic cell markers.

In some aspects, the cells are transfected with a gene capable of stimulating angiogenesis. In some aspects, the gene capable of stimulating angiogenesis is selected from the group of soluble growth factors consisting of: VEGF, FGF-1, FGF-2, FGF-4, EGF, and HGF. In some aspects, the gene capable of stimulating angiogenesis is selected from a group of transcription factors consisting of: HIF-1α, HIF-2, NET, and NF-kB.

In certain aspects of the above embodiments, the cells are induced to upregulate angiogenic potential. In some aspects, the induction is performed by culturing under a singular or plurality of conditions selected from a group consisting of: hypoxia, small molecule treatment, radiation treatment, and cytokine treatment. In certain aspects, the cells are treated under conditions to enhance migration to areas of hypoxia. In certain aspects, the cells are programmed to undergo enhanced migration through gene transfection with receptors for chemotactic ligands selected from a group consisting of: CXCR-4, VEGF-R1, VEGF-R2, and CCR1.

In certain aspects of the above embodiments, the cells are administered in a manner to allow migration to the area of hypoperfusion. In certain aspects, the said cells are administered into the lumbar associated muscles. In certain aspects, the cells are administered into the psoas major muscle. In certain aspects, the cells are administered into the multifidus muscle. In certain aspects, the cells are administered into the multifidus muscle, transversospinalis muscle, or sacrospinalis muscle.

In certain aspects where a matrix is administered, the matrix is capable of sustaining cellular viability and temporary localization to the area of injection. In certain aspects, the matrix is chosen from a group consisting of: a collagen derivative, a hydrogel, calcium alginate, agarose, hyaluronic acid, a poly-lactic/poly-glycolic acid derivative and fibrin. In certain aspects, the matrix contains a growth factor. The growth factor can be chosen from a group consisting of: IGF, EGF, (TGF-beta, acidic and basic fibroblast growth factor, FGF-4, activin A, BMP, PDGF, insulin, erythropoietin, PDGF, HGF, placental growth factor, keratinocyte growth factor; HBGF-1, HBGF-2, GDF, CSF-1, G-CSF, and GM-CSF. In certain aspects, the growth factor is comprised of a culture supernatant. In certain aspects, the culture supernatant is derived from culturing of a stem cell, an endothelial cell, or a combination of cells. In certain aspects, the cells are cultured under conditions stimulatory of angiogenic factors chosen from a group consisting of: hypoxia, gene transfer with angiogenic factors, and co-culture with other cells.

Also provided herein is a method for ameliorating pain and preventing the progress of disc degenerative disease comprising: a) administering a cell capable of stimulating angiogenesis in a manner allowing access of said cell capable of stimulating angiogenesis to induce formation of blood vessels so as to increase general perfusion of area associated with disc degeneration; and b) administering a cell capable of inhibiting inflammatory responses in a manner allowing access of said cell capable of inhibiting inflammatory responses to substantially suppress inflammatory responses causative of pain and said disc degenerative disease.

In certain aspects, the cell capable of stimulating angiogenesis is autologous, allogeneic, or xenogeneic in respect to intended recipient of said cells. In certain aspects, the cell capable of stimulating angiogenesis possesses properties to enable growth, generation or redistribution of blood vessels at a more rapid rate as compared to if said cell was not administered. In certain aspects, the cell capable of stimulating angiogenesis expresses growth factors, matrix metalloproteases, chemoattractant functions, or other biological properties needed for formation of new blood vessels. In certain aspects, the cell capable of stimulating angiogenesis is selected from a group consisting of: mesenchymal stem cells; b) hematopoietic stem cells; c) cord blood progenitor cells; d) embryonic stem cells; e) endothelial stem cells; f) adipose derived stem cells; and g) placenta derived stem cells.

Also provided herein is a method for ameliorating pain and preventing the progress of disc degenerative disease comprising administration of a singularity or plurality of cells capable of inhibiting inflammatory responses to substantially suppress inflammatory responses causative of pain and said disc degenerative disease.

In certain aspects, the cell capable of inhibiting inflammatory responses is selected from a group consisting of: cells expressing the CD4+ CD25+ phenotype and possessing T cell inhibitory function; cells concurrently expressing a T cell receptor and one or more markers found on natural killer cells and possessing ability to produce interleukin-4; myeloid progenitor cells expressing the marker CD31, and/or CD34, and/or Gr-1, and/or having affinity to wheat germ agglutinin, and possessing ability to inhibit proliferation of activated T cells; immature dendritic cells expressing lower levels of MHC II, and/or CD80, and/or CD86 in comparison to mature dendritic cells and having a lower allostimulatory activity as compared to mature dendritic cells.

In certain aspects, the cells expressing the CD4+ CD25+ phenotype and possessing T cell inhibitory function are purified from a group of sources consisting of: peripheral blood, cord blood, and bone marrow. In certain aspects, the cells expressing the CD4+ CD25+ phenotype and possessing T cell inhibitory function are expanded by stimulation with agents known to trigger proliferation, and/or enhancement of T cell suppressing activity in a physiologically relevant manner. In certain aspects, the cells expressing the CD4+ CD25+ phenotype and possessing T cell inhibitory function are expanded by stimulation with a singular or plurality of agents selected from a group consisting of: IL-2, TGF-beta, IL-10, anti-CD3 antibodies, anti-CD28 antibodies, vasoactive intestinal peptide and anti-PD1 antibodies. In certain aspects, the cells expressing the CD4+ CD25+ phenotype and possessing T cell inhibitory function are expanded by co-culture with monocytes and stimulation with a singular or plurality of agents selected from a group consisting of: IL-2, TGF-beta, IL-10, anti-CD3 antibodies, anti-CD28 antibodies, vasoactive intestinal peptide and anti-PD1 antibodies. In certain aspects, the cells expressing the CD4+ CD25+ phenotype and possessing T cell inhibitory function are expanded by co-culture with dendritic cells and stimulation with a singular or plurality of agents selected from a group consisting of: IL-2, TGF-beta, IL-10, anti-CD3 antibodies, anti-CD28 antibodies, vasoactive intestinal peptide and anti-PD1 antibodies.

In certain aspects, the cells concurrently expressing a T cell receptor and one or more markers found on natural killer cells and possessing ability to produce interleukin-4 are natural killer T cells. In certain aspects, the natural killer T cells are purified from a group of sources consisting of: peripheral blood, cord blood, and bone marrow. In certain aspects, the natural killer T cells are expanded by stimulation with agents known to trigger proliferation, and/or enhancement of T cell suppressing activity in a physiologically relevant manner. In certain aspects, the natural killer T cells are expanded by stimulation with a singular or plurality of agents selected from a group consisting of: lenalidomide, alpha-galactosyl-ceramide, IL-15, IL-7, Flt3-L and IL-2. In certain aspects, the natural killer T cells are expanded by co-culture with monocytes and stimulation with a singular or plurality of agents selected from a group consisting of: lenalidomide, alpha-galactosyl-ceramide, IL-15, IL-7, Flt3-L and IL-2. In certain aspects, the natural killer T cells are expanded by co-culture with dendritic cells and stimulation with a singular or plurality of agents selected from a group consisting of: lenalidomide, alpha-galactosyl-ceramide, IL-15, IL-7, Flt3-L and IL-2.

In certain aspects, the myeloid progenitor cells expressing the marker CD31, and/or CD34, and/or Gr-1, and/or having affinity to wheat germ agglutinin, and possessing ability to inhibit proliferation of activated T cells are purified from a group of sources consisting of: peripheral blood, cord blood, and bone marrow. In certain aspects, the myeloid progenitor cells are expanded by stimulation with agents known to trigger proliferation, and/or enhancement of T cell suppressing activity in a physiologically relevant manner. In certain aspects, the myeloid progenitor cells are expanded by stimulation with a singular or plurality of agents selected from a group consisting of: TGF-b, IL-10, vitamin D3, G-CSF, M-CSF, GM-CSF, flt-3L, and IL-3.

In certain aspects, the immature dendritic cells expressing lower levels of MHC II, and/or CD80, and/or CD86 in comparison to mature dendritic cells and having a lower allostimulatory activity as compared to mature dendritic cells are expanded from progenitor cells. In certain aspects, the progenitor cells for generating cells immature dendritic cells are purified from a group of sources consisting of: peripheral blood, cord blood, and bone marrow. In certain aspects, the differentiation of said progenitor cells into immature dendritic cells is performed using a culture system containing agents known to block the dendritic cell differentiation process, together with agents acting as mitogenic stimuli for expansion. In certain aspects, the agents inhibiting differentiation are selected from a group consisting of: IL-4, IL-10, IL-13, IL-20, TGF-beta, NF-kB inhibitors, Janus Activated Kinase inhibitors, inhibitors of signal transducers and activators of transcription, and inhibitors of T-bet. In certain aspects, the agents acting as mitogens for expansion are selected from a group consisting of: G-CSF, GM-CSF, flt-3L, human serum, fetal calf serum, and cord blood serum.

In certain aspects, the combination of angiogenesis stimulating cells and anti-inflammatory cells are administered concurrently, sequentially, or in various combinations in order to induce increased angiogenesis of the lumbar area in a patient in need thereof, while also inhibiting inflammatory processes. In certain aspects, the anti-inflammatory cells are administered systemically and said angiogenesis stimulating cells are administered locally. In certain aspects, the anti-inflammatory cells are administered systemically and/or locally to the area of pain generation.

Also provided herein is a method of treating lower back pain through administration of non-angiogenic cells rendered with angiogenic potential through gene transfection.

Also provided herein is a method of accelerating healing of disc resorption through the method of the above embodiments.

Also provided herein is a method of accelerating proteoglycan synthesis after chemonucleolysis through the method of the above embodiments.

Also provided herein is a method of treating lower back pain through localized administration of small interfering RNA specific to an inflammatory stimulus or stimuli, with the concurrent administration of cells capable of stimulating angiogenesis. In certain aspects, the short interfering RNA is capable of substantially silencing expression of a protein. In certain aspects, the said short interfering RNA is capable of substantially silencing expression of a transcription factor. In certain aspects, the short interfering RNA is capable of substantially silencing expression of a protein selected from: IL-1, TNF, IL-2, IL-6, IL-7, IL-8, MCP-1, IL-11, IL15, IL-18, IL23, IL-21, and IL-27. In certain aspects, the short interfering RNA is capable of substantially silencing expression of a transcription factor selected from: NF-kB, IRF-3, STAT1, STAT2, STAT3, STAT4, and T-bet.

Also provided herein is a cellular composition for use in the inhibition and/or reversal of disc degeneration comprising administration of cells capable of augmenting the rate of perfusion to the area of disc degeneration. In certain aspects, the cells can be autologous, allogeneic or xenogeneic. In certain aspects, the cells are substantially composed of stem cells. In certain aspects, the stem cells are selected from a group comprising a side population, embryonic, germinal, endothelial, hematopoietic, myoblast, placental, cord-blood, adipocyte and mesenchymal stem cells. In certain aspects, the wherein side population stem cells are identified based on expression multidrug resistance transport protein (ABCG2) or ability to efflux intracellular dyes such as rhodamine-123 and or Hoechst 33342. In certain aspects, the embryonic stem cells are identified based on expression of one or more antigens selected from a group consisting of: stage-specific embryonic antigens (SSEA) 3, SSEA 4, Tra-1-60 and Tra-1-81, Oct-3/4, Cripto, gastrin-releasing peptide (GRP) receptor, podocalyxin-like protein (PODXL), and human telomerase reverse transcriptase (hTERT). In certain aspects, the germinal stem cells are identified based on expression of one or more antigens selected from a group consisting of: SSEA-4, GCTM-2 antigen, TRA 1-60, Cripto, gastrin-releasing peptide (GRP) receptor, podocalyxin-like protein (PODXL), and human telomerase reverse transcriptase (hTERT). In certain aspects, the endothelial stem are identified based on expression of one or more antigens selected from a group consisting of: CD31, CD34, AC133, CD146 and flk1. In certain aspects, the hematopoietic stem cells are identified based on expression of one or more antigens selected from a group consisting of: CD34, c-kit, flk-1, and CXCR-4. In certain aspects, the myoblast stem cells are identified based on expression of one or more antigens selected from a group consisting of: Pax7, MyoD, and AC133. In certain aspects, the placental stem cells are identified based on expression of one or more antigens selected from a group consisting of: Oct-4, Rex-1, CD9, CD13, CD29, CD44, CD166, CD90, CD105, SH-3, SH-4, TRA-1-60, TRA-1-81, SSEA-4 and Sox-2. In certain aspects, the cord blood stem cells are identified based on expression of one or more antigens selected from a group consisting of: CD34, c-kit, and CXCR-4. In certain aspects, the adipocyte stem cells are identified based on expression of one or more antigens selected from a group consisting of: CD13, CD29, CD44, CD63, CD73, CD90, CD166, Aldehyde dehydrogenase (ALDH), and ABCG2. In certain aspects, the mesenchymal stem cells are identified based on expression of one or more antigens selected from a group consisting of: STRO-1, CD105, CD54, CD106, HLA-I markers, vimentin, ASMA, collagen-1, and fibronectin, but not HLA-DR, CD117, and hemopoietic cell markers.

In certain aspects, the cells are cells transfected with a gene capable of stimulating angiogenesis. In certain aspects, the gene capable of stimulating angiogenesis is selected from a group of soluble growth factors consisting of: VEGF, FGF-1, FGF-2, FGF-4, EGF, and HGF. In certain aspects, the gene capable of stimulating angiogenesis is selected from a group of transcription factors consisting of: HIF-1α, HIF-2, NET, and NF-kB.

DETAILED DESCRIPTION

The invention capitalizes on the naturally occurring healing processes that are ineffective in patients with lower back disorders, and augments these processes to reduce pain and augment regeneration. Ineffective healing processes may be due to ischemia of the lower back area caused by atherosclerosis, and/or inflammatory processes that are associated with degenerated discs. More specifically, the invention relates to methods of increasing angiogenesis using cellular therapy in the lower back area in order to accelerate the healing processes and induce regeneration through endogenous and/or exogenously derived stem cells. Furthermore, the invention provides procedures, processes and cell types useful for inhibiting inflammation either through administration of said cells alone or together with other cells to substantially enhance the angiogenesis and healing process. The invention can be practiced in a variety of medically relevant conditions, including, but not limited to disc degeneration, disc prolapse, and lumbar pain.

Disc Degeneration

Disc degeneration can begin as early as the first decade of life when various biochemical changes become apparent in the endplate and the nucleus pulposus (Benoist, M. 2003. *Eur Spine J* 12 Suppl 2:S86-89, which is incorporated by reference herein in its entirety). Subsequently, in the second decade notochordal cells begin undergoing replacement by chondrocytes. In the third decade loss of the fine fibrous connective tissue network and replacement by hyalinized collagen fibers occurs, with concurrent initiation of fissures in the annulus fibrosus. Beginning in the forth decade and almost always present in the fifth is replacement of the nucleus pulposus jelly-like substance with a fibrous collagen type II structure that resembles the annulus fibrosus. By the seventh decade the nucleus pulposus is completely devoid of the water carrying proteoglycan mass and instead is empty or filled with amorphous material. During this natural process the cartilage endplate, which contains blood vessels for the annular fibrosus and nucleus pulposus becomes replaced with fibrocartilage and blood flow progressively diminishes. Since the only 2 routes for the exchange of solutes with the blood vessels outside the disk are via the periphery of the annulus, and through the endplates, the natural degeneration of the endplate blood supply causes a decrease ability of nucleus pulposus cells to function/survive, thus leading to decreased proteoglycan synthesis and disc degeneration (Urban, et al. 1977. *Clin Orthop Relat Res:*101-114, which is incorporated by reference herein in its entirety).

The synthesis of proteoglycans in the nucleus pulpous occurs naturally by the cellular component of the nucleus pulposus. Specific growth factors such as TGF-b and EGF are involved in the stimulation of proteoglycan synthesis. Interestingly in patients with degenerative disc disease the amount of these cytokines is reduced in comparison to healthy nucleus pulposus cells (Konttinen, et al. 1999. *J Bone Joint Surg Br* 81:1058-1063, which is incorporated by reference herein in its entirety). Another reason for inhibition of proteoglycan synthesis is lower pH caused by ischemia of the lumbar area (Razaq, et al. 2003. *Eur Spine J* 12:341-349, which is incorporated by reference herein in its entirety). On the other hand, it is known that matrix metalloproteases are involved in cleaving proteoglycans, and that upregulation of matrix metalloprotease activity is associated with disc degeneration (Gruber, et al. 2005. *Biotech Histochem* 80:157-162, which is incorporated by reference herein in its entirety). Activation of matrix metalloproteases is known to be induced by inflammatory cytokines such as TNF and IL-1 (Seguin, et al. 2005. *Spine* 30:1940-1948, which is incorporated by reference herein in its entirety). Additionally, animal studies have demonstrated that hyperphysiological loading of the disc segment induces upregulation of matrix metalloproteases (Omlor, et al. 2006. *J Orthop Res* 24:385-392, which is incorporated by reference herein in its entirety).

Therefore it appears that lower back pain, at least in a large proportion of patients, is caused by an inflammatory event that occurs in conjunction with lumbar disc degeneration. The link between inflammation and pain is established in studies showing that radiologically degenerated discs are not associated with main in a large number of subjects. In contrast, the presence of localized inflammation associated with disc degeneration, as exemplified by the presence of granulation tissue which is believed to be causative of nociception and the symptoms of chronic, intractable, lower back pain (Peng et al. 2005, supra; Hwang, et al. 1997. *J Magn Reson Imaging* 7:575-578, each of which is incorporated by reference herein in its entirety).

Current Treatments

Although disc degeneration continues to have a tremendous and ever-increasing impact worldwide, current treatment options do not address the underlying cause. These include bed rest, nonsteroidal anti-inflammatory medication in the early phases of pathology, and procedures such as discectomy, arthroplasty (joint replacement), injection of artificial nucleus pulposus and fusion in the later phases when the prior approaches did not ameriorate pain. Approaches such as the previously mentioned not only are unpredictable, but also deal almost exclusively with end-stage clinical manifestations, and therefore do nothing to alter the disease process itself. Additionally, procedures such as vertebral fusion result in the increased incidence of disc degeneration in the adjacent discs due to alterations in the biomechanical distribution of work-load.

Recent advances in both biotechnology and our understanding of the biochemical makeup and environment of the intervertebral disc have led to increased interest in the process of degeneration and the possibility of developing novel treatments aimed directly at disc preservation. Certain genes found to have significant impact on matrix synthesis and catabolism within the disc have provided targets for scientists seeking to alter the balance between the two. To this end, much attention over the past several years has centered on gene therapy, and these efforts have yielded promising preclinical results with regard to its use in treating disc degeneration (Levicoff, et al. 2005. *Spine J* 5:287S-

296S, which is incorporated by reference herein in its entirety). Unfortunately, none of these approaches are near clinical implementation at the time of writing. Additionally, it is important to note that even in the circumstance that disc regeneration alone can be achieved through gene-therapy or other interventional means, the underlying process that originally caused the degeneration must be addressed in order to prevent re-occurrence.

Biological Treatments

Currently, no biologic treatment is widely available for disc degeneration. However, many different molecules of potential therapeutic benefit are being investigated. The focus of molecular therapy has been to prevent or reverse one or more aspects of these changes in the disc extracellular matrix. At least four different classes of molecules may be effective in disc repair. These include anticatabolics, mitogens, chondrogenic morphogens and intracellular regulators (Yoon, S. T. 2005. Spine J 5:280S-286S; Masuda, et al. 2004. Spine 29:2757-2769; Shimer, et al. 2004. Spine 29:2770-2778, each of which is incorporated by reference herein in its entirety).

As mentioned above, hallmarks of disc degeneration include loss of proteoglycan, water, and Type II collagen in the disc matrix. Furthermore, qualitative changes in the matrix are less well defined, including loss of the higher molecular weight proteoglycans, and other changes that are more difficult to quantify (collagen crosslinking, organization of the proteoglycan, etc). An important process in disc degeneration seems to be the change of the differentiated chondrocyte phenotype in the nucleus pulposus into a more fibrotic phenotype. Together these changes in the disc matrix lead to alteration of the disc and vertebral anatomy that ultimately is associated with a pathologic condition (Setton, et al. 2004. Spine 29:2710-2723; Roughley, P. J. 2004. Spine 29:2691-2699, each of which is incorporated by reference herein in its entirety).

Because matrix loss is a balance between matrix synthesis and degradation, it is possible to increase disc matrix by increasing synthesis or by decreasing degradation. One approach is to prevent matrix loss by inhibiting the degradative enzymes.

Degenerated discs have elevated concentrations of matrix metalloproteinases (MMPs). Within the matrix, MMP activity is normally inhibited by tissue inhibitors of MMPs (TIMPs) (Roberts, et al. 2000. Spine 25:3005-3013; Nagase, et al. 1999. J Biol Chem 274:21491-21494; Wallach, et al. 2003. Spine 28:2331-2337, each of which is incorporated by reference herein in its entirety). Wallach et al tested whether one of these anticatabolic molecules, TIMP-1, could increase the accumulation of matrix proteoglycans with in vitro experiments. The researchers found that indeed TIMP-1 expression in disc cells increased accumulation and also increased the "measured synthesis rate" of proteoglycans (Wallach et al., supra).

Chondrogenic morphogens are cytokines that not only possess mitogenic capability but are characterized by their ability to increase the chondrocyte-specific phenotype of the target cell. Most of the research in chondrogenic morphogens has been with transforming growth factor-b (TGF-b), bone morphogenetic proteins (BMPs) or growth and differentiation factors (GDFs). Chondrogenic morphogens are particularly attractive because they may reverse the fibrotic phenotype of disc cells to the more chondrocytic phenotype of disc nucleus cells in younger and more "normal" discs. By definition, these molecules are secreted molecules and hence can potentially act in autocrine, paracrine and endocrine fashion. TGF-b1 is one of the first disc morphogenic molecules to be studied. Thompson et al. reported that TGF-b1 was a mitogen but also showed that it was a highly anabolic molecule leading to significantly increased proteoglycan synthesis per cell. Gene transfer of TGF-b using an adenoviral/CMV vector was capable of reversing radiological signs of disc degeneration in a rabbit model (Zhan, et al. 2004. J Huazhong Univ Sci Technolog Med Sci 24:599-601, 624, which is incorporated by reference herein in its entirety).

BMP-2 is another prototypic chondrogenic morphogen (Thompson, et al. 1991. Spine 16:253-260, which is incorporated by reference herein in its entirety). Yoon et al. reported that recombinant human BMP-2 increased production of rat disc cell proteoglycan and significantly increased the chondrocytic phenotype of the disc cells as shown by increased aggrecan and Type II collagen gene expression, whereas there was no change in Type I collagen gene expression (Yoon, et al. 2004. Spine 29:2603-2611, which is incorporated by reference herein in its entirety). Kim et al. reported that BMP-2 can partially reverse the inhibitory effect of nicotine on the synthesis of disc cell proteoglycan (Kim, et al. 2003. J Neurosurg 99:291-297, which is incorporated by reference herein in its entirety). BMP-7, also known as OP-1 (osteogenic protein-1), is another disc cell morphogen that has demonstrated potent in vitro activity in terms of enhancing matrix formation in disc cells (Masuda, et al. 2003. J Orthop Res 21:922-930; Zhang, et al. 2004. Am J Phys Med Rehabil 83:515-521; Takegami, et al. 2002. Spine 27:1318-1325, each of which is incorporated by reference herein in its entirety). GDF-5 is also known as CDMP-1 is also considered for regeneration of disc cells, although only in vitro experimentation has occurred (Chang, et al. 1994. J Biol Chem 269:28227-28234, which is incorporated by reference herein in its entirety).

Intracellular regulators are a distinct class of molecules because they are not secreted molecules and do not work through transmembrane receptors. These molecules are neither cytokines nor growth factors in the classical sense, and yet they can have effects that are quite similar to the secreted molecules discussed previously. This class of molecules typically controls one or more aspects of cellular differentiation. For instance, Sma-Mad (Smad) proteins are intracellular molecules that mediate BMP-receptor signalling (Nohe, et al. 2004. Cell Signal 16:291-299; Hatakeyama, et al. 2003. J Bone Joint Surg Am 85-A Suppl 3:13-18, each of which is incorporated by reference herein in its entirety). Although there are no specific published papers on the effect of Smad proteins on disc cells, SMAD proteins such as Smad-1 and Smad-5 are predicted to induce similar effects on disc cells as BMP-2, such as increasing proteoglycan and Type II collagen synthesis. Sox9 is a chondrocyte marker that is a positive regulator of Type II collagen mRNA transcription (Yoon 2005, supra; Li, et al. 2004. Tissue Eng 10:575-584; Aigner, et al. 2003. Matrix Biol 22:363-372, each of which is incorporated by reference herein in its entirety). Paul et al. showed that Sox9 delivered by adenovirus can increase Sox9 expression and disc cell production of Type II collagen in in vitro experiments (Paul, et al. 2003. Spine 28:755-763, which is incorporated by reference herein in its entirety).

The success of a disc tissue engineering strategy is dependent on molecular cues to direct the differentiation of cells and affect their biosynthetic function. Many growth factors, including members of the transforming growth factor beta superfamily affect the differentiation process of disc cells. This group of related proteins directs the induction of mesenchymal precursors to form mature skeletal tissues (Sampath, et al. 1984. *Proc Natl Acad Sci USA* 81:3419-3423, which is incorporated by reference herein in its entirety). The activity of these molecules is complex and affects intercellular signaling pathways (Israel, et al. 1996. *Growth Factors* 13:291-300; Heldin, et al. 1997. *Nature* 390:465-471, each of which is incorporated by reference herein in its entirety). In addition, concentration and timing of presentation of the growth factor influences its activity. Depending on the tissue, the effects of a given morphogen may be different. For instance, the osteogenic molecule bone morphogenetic protein-7-osteogenic protein-1 (BMP-7/OP-1) has been shown to have a dramatic effect on disc cells, increasing their metabolic output of matrix proteins and rescuing them from the detrimental effects of IL-1 (Takegami et al., supra). This data suggests that growth factors could play a useful role in a cell-based tissue engineering strategy.

Other yet to be identified factors direct cell-to-cell communication and appear to play an important role in the viability and metabolic activity of disc cells. Yamamoto et al. showed that cell proliferation and proteoglycan synthesis was significantly enhanced in disc cells cultured in a system that allowed direct cell-cell contact with bone marrow-derived stromal cells (Yamamoto, et al. 2004. *Spine* 29:1508-1514, which is incorporated by reference herein in its entirety). In another study, Hunter et al. reported that enzymatic disruption of gap junctions produced a negative effect on cell viability, suggesting that cellular communication plays a vital role in cell viability and function, and therefore interventions supporting their enhancement may be beneficial (Hunter, et al. 2004. *Spine* 29:1099-1104, which is incorporated by reference herein in its entirety).

Although the above studies provide insight into the molecular processes of disc degeneration, they do not seek to address the underlying cause and progression. Current evidence strongly suggests that the main causative factor in back pain associated with disc degeneration, and the transformation of degeneration into a painful syndrome is lack of perfusion to the lumbar area caused by atherosclerotic lesions. The potent influence of perfusion in degeneration is seen in animal models where the smoking induced reduction of lumbar perfusion rapidly correlates with degeneration (Iwahashi, et al. 2002. *Spine* 27:1396-1401, which is incorporated by reference herein in its entirety). Additional evidence for the importance of perfusion in degeneration is provided below.

Role of Poor Perfusion

Numerous studies clearly demonstrated that the vast majority of patients with long-term lower back pain, intractable by conventional approaches, have occluded lumbar/middle sacral arteries and that occlusion of these arteries is associated with disc degeneration (Kauppila, et al. 2004. *Spine* 29:2147-2152, which is incorporated by reference herein in its entirety). Degree of occlusion is so marked that visualization can be made by standard angiography. Furthermore, patients with high LDL cholesterol complained of more severe back symptoms than those with normal value (Kauppila, et al. 2004. *Spine* 29:2147-2152). These findings support previous studies that occlusion of lumbar/middle sacral arteries is associated with lower back pain and disc degeneration (Kauppila, L. I. 1995. *Lancet* 346:888-889; Boggild, H. 2006. *Scand J Work Environ Health* 32:20-21; Kauppila, et al. 1993. *J Spinal Disord* 6:124-129; Kauppila, et al. 1997. *Spine* 22:1642-1647; Kurunlahti, et al. 1999. *Spine* 24:2080-2084, each of which is incorporated by reference herein in its entirety) and that occlusion of these arteries may be due to atherosclerosis (Cluroe, et al. 1992. *Pathology* 24:140-145; Kauppila, et al. 1994. *Spine* 19:923-929, each of which is incorporated by reference herein in its entirety). Epidemiologic and post-mortem studies indicate that atheromatous lesions in the abdominal aorta may be related to disc degeneration and long-term back symptoms (Kauppila, L. I. 1995. *Lancet* 346:888-889; Boggild, H. 2006. *Scand J Work Environ Health* 32:20-21; Kauppila, et al. 1993. *J Spinal Disord* 6:124-129; Kauppila, et al. 1997. *Spine* 22:1642-1647; discussion 1648-1649; Kurunlahti, et al. 1999. *Spine* 24:2080-2084, each of which is incorporated by reference herein in its entirety).

The blood supply of the lumbar spine is derived from the aorta through the lumbar and middle sacral arteries. The upper four segments of the lumbar spine receive their blood supply from the four pairs of the lumbar arteries, which arise in the posterior wall of the abdominal aorta. The fifth lumbar segment is supplied partly by the middle sacral artery (arising in the bifurcation) and partly by branches of the iliolumbar arteries (arising from the internal iliac arteries) (Crock H V, Y.H.T.B.S.o.t.V.C.a.S.C.i.M.N.Y.S.-V., 1977; Kauppila, L. I. 1994. *Acta Radiol* 35:541-544, each of which is incorporated by reference herein in its entirety).

Nutrition of the avascular intervertebral disc occurs by diffusion through the vertebral endplates from the blood vessels in the vertebral bodies above and below the disc (Urban, et al. 2004. *Spine* 29:2700-2709; Walker, et al. 2004. *Spine J* 4:158S-166S, each of which is incorporated by reference herein in its entirety). Cholesterol plaques in the wall of the aorta obliterate orifices of lumbar and middle sacral arteries and decrease blood supply of the lumbar spine and its surrounding structures. As a result, structures with precarious nutrient supply, such as the intervertebral discs, gradually degenerate (Cluroe et al., supra; Mitchell, et al. 1977. *Atherosclerosis* 27:437-446; Ross R. Atherosclerosis. In: Wyngaarden J B, S. L., eds. Cecil's Textbook of Medicine. Philadelphia: Saunders, 1988:318-23. 13., each of which is incorporated by reference herein in its entirety). Reduced blood flow causes hypoxia and tissue dysfunction. It also hampers removal of waste products, such as lactic acid. These changes in turn may irritate nociceptive nerve endings, causing pain, as well as lead to deterioration and atrophy of the structures involved (Naves, et al. 2005. *Braz J Med Biol Res* 38:1561-1569; Iwabuchi, et al. 2001. *Spine* 26:1651-1655; Ohshima, et al. 1992. *Spine* 17:1079-1082; Bibby, et al. 2004. *Eur Spine J* 13:695-701, each of which is incorporated by reference herein in its entirety).

Angiogenesis

The process of new blood vessel formation can occur through 3 various means, namely: Vasculogenesis, arteriogenesis, and angiogenesis. For the purpose of this invention, all three will be referred to as "angiogenesis", despite the fact that this definition is technically incorrect. Technically speaking, angiogenesis is strictly associated with de novo capillary formation from post-capillary venules, is ischemia-driven, and associated with a 2-3 fold increase in blood flow. Arteriogenesis is technically considered remodeling of pre-existing vascular channels or de novo artery formation, it is stimulated by local changes in perfusion, as well as cellular influx, and associated with a 20-30 fold increase in blood flow. Vasculogenesis is technically considered do novo formation or remodeling of pre-existing vascular channels initiated by circulating vascular precursor cells, furthermore it is considered to be ischemia and injury initiated (Simons, M. 2005. *Circulation* 111:1556-1566, which is incorporated by reference herein in its entirety). We chose to use the term "angiogenesis" to encompass all three technical terms due to functional uncertainty at present regarding the continuum of differences between these sub-divisions.

Angiogenesis is known to occur physiologically during implantation/embryogenesis (Sharkey, et al. 2005. *Contraception* 71:263-271, which is incorporated by reference herein in its entirety), wound healing (Dvorak, H. F. 2005. *J Thromb Haemost* 3:1835-1842, which is incorporated by reference herein in its entirety), and expansion of adipose mass (Voros, et al. 2005. *Endocrinology* 146:4545-4554, which is incorporated by reference herein in its entirety). Pathologically, uncontrolled angiogenesis is associated with a variety of diseases such as macular degeneration (Kroll, et al. 2006. *Br J Ophthalmol* 90:128-130, which is incorporated by reference herein in its entirety), cancer (Folkman, J. 2002. *Semin Oncol* 29:15-18, which is incorporated by reference herein in its entirety), arthritis (Maruotti, et al. 2006. *Histol Histopathol* 21:557-566, which is incorporated by reference herein in its entirety), and atherosclerosis (Conway, E. M. 2003. *Pathophysiol Haemost Thromb* 33:241-248, which is incorporated by reference herein in its entirety). One common aspect of adult angiogenesis is the issue of tissue hypoxia. In all situations of tissue expansion, cells are dependent on the microvasculature for nutrients and oxygen supply, as well as removal of metabolic waste products. Accordingly during tissue growth, cells begin to "sense" a lack of oxygen, this triggers a cascade of events that culminate in angiogenesis.

Although numerous methods of physiological stimulation of angiogenesis under hypoxia are known (Mizukami, et al. 2006. *J Biol Chem.*, which is incorporated by reference herein in its entirety), one of the most well characterized pathways involves activation of the Hypoxia Inducible Factor (HIF)-1, transcription factor (Liu, et al. 2004. *Cancer Biol Ther* 3:492-497, which is incorporated by reference herein in its entirety). This protein is only functionally active as a heterodimer consisting of HIF-1a and HIF-1b, which are both basic helix-loop-helix proteins. While the latter is known to be relatively stable, the former has a half-life of less than 5 minutes under physiological conditions due to rapid proteasomal degradation by the oxygen sensitive von Hippel-Lindau (VHL) E3-ubiquitin ligase system (Ivan, et al. 2001. *Science* 292:464-468, which is incorporated by reference herein in its entirety). When cells experience hypoxia, HIF-1-alpha half-life is increased since the degradation by VHL E3-ubigitine ligase is dependent on proline hydroxylation, which requires molecular oxygen. Therefore this protein modification plays a key role in mammalian oxygen sensing. Activation of this transcription factor leads to gene expression of numerous angiogenesis related genes such as VEGF (Gray, et al. 2005. *Oncogene* 24:3110-3120, which is incorporated by reference herein in its entirety), FGF-2 response genes (Li, et al. 2002. *J Cell Sci* 115:1951-1959, which is incorporated by reference herein in its entirety), notch signaling (Pear, et al. 2005. *Cancer Cell* 8:435-437, which is incorporated by reference herein in its entirety), and upregulation of stromal derived factor (SDF-1) production which chemoattracts endothelial precursors during angiogenesis (Ceradini, et al. 2005. *Trends Cardiovasc Med* 15:57-63, which is incorporated by reference herein in its entirety). There are numerous variations by which angiogenesis can occur, however the basic steps involve remodeling of the extracellular matrix through matrix metalloproteases (MMPs), chemoattraction of either precursor endothelial cells or existing endothelial cells from an adjacent vesses, proliferation of the endothelial cells, tube formation and stabilization. For detailed descriptions the reader is referred to the following review articles (Zhong, et al. 2006. *Curr Med Chem* 13:849-862; Gruber, et al. 2006. *Curr Opin Hematol* 13:169-174; Springer, M. L. 2006. *Curr Opin Investig Drugs* 7:243-250, each of which is incorporated by reference herein in its entirety).

Therapeutic Angiogenesis: Growth Factor Therapy

Numerous studies have demonstrated angiogenesis inhibition to be beneficial in the treatment of cancer in animal models for the last 3 decades, however it was only in 2005 that the first clinical angiogenesis intervention (Avastin) was approved by the FDA for treatment of cancer. Even this approval was only for metastatic colorectal cancer, and only in combination with the chemotherapeutic drug 5-fluorouracil. The difficulty with translating animal data into the clinic was based upon intrinsic differences in tumor physiology between the experimental and clinical situations.

On the opposite end of the spectrum, angiogenesis stimulation as a therapy has also been explored. Originally, stimulation of angiogenesis was therapeutically used in patients with advanced angina, with the hope of increasing myocardial perfusion. Intramyocardial administration of recombinant FGF-1 protein was performed in patients undergoing coronary artery bypass grafting. In 20 patients treated with FGF-1 a significant increase in myocardial perfusion was noted in comparison to 20 control patients (Stegmann, T. J. 1998. *Expert Opin Investig Drugs* 7:2011-2015, which is incorporated by reference herein in its entirety). Other attempts to induce therapeutic angiogenesis have also been performed using VEGF administration. This growth factor, while inducing rapid formation of large blood vessels, causes their disorganization and lack of appropriate pericyte support, resulting in "leaky vessels". Despite this, some improvement in exercise time at 120 days was noted in patients administered VEGF protein but not placebo controls in a double-blind study (Henry, et al. 2003. *Circulation* 107:1359-1365, which is incorporated by reference herein in its entirety).

Therapeutic angiogenesis also has promise in conditions such as critical limb ischemia (CLI) which is caused by atherosclerotic plaque built-up on the femoral and inguinal arteries. A safety and efficiency, prospective open-label study was conducted of the angiogenic stimulant hepatocyte growth factor (HGF) administered has plasmid DNA intramuscularly to 6 patients with CLI Fontaine III or IV. Reduction of pain scale of more than 1 cm in visual analog pain scale was observed in 5 of 6 patients, and increase in ankle pressure index more than 0.1 was observed in 5 of 5 patients. Additionally, the long diameter of 8 of 11 ischemic ulcers in 4 patients was reduced >25% (Morishita, et al. 2004. *Hypertension* 44:203-209, which is incorporated by reference herein in its entirety). In another study, gene transfer of naked plasmid DNA encoding the 165-amino-acid isoform of VEGF was injected directly into the muscles 9 patients with ischemic limbs. The ankle-brachial index improved significantly and newly visible collateral blood vessels were directly documented by contrast angiography in 7 limbs. Using magnetic resonance angiography a demonstration was made of qualitatively enhanced distal flow in 8 limbs. At a clinical level, ischemic ulcers healed or markedly improved in 4 of 7 limbs, including successful limb salvage in 3 patients recommended for below-knee amputation. Histological evidence of angiogenesis was provided by observation of tissue specimens obtained from an amputee 10 weeks after therapy, which showed areas of proliferating endothelial cells by immunohistochemistry (Baumgartner, et at. 1998. *Circulation* 97:1114-1123, which is incorporated by reference herein in its entirety).

Therapeutic Angiogenesis: Cell Therapy

As noted above, the angiogenic cascade involves numerous proteins and growth factors acting in concert to promote generation of functional blood vessels. The importance of physiologically administering the growth factors under appropriate conditions is illustrated in studies where administration of VEGF results in leaky vessels. An example of the relevance of homeostatically delivering angiogenic agents is provided by Ehrbar et al, who engineered a type of VEGF that is only released when adjacent cells require it. Specifically, the authors generated a alpha2PI1-8-VEGF121 protein which is active only when cleaved by matrix metalloproteases or plasmin. When this protein was administered in a fibrin gel, organized, non-leaky blood vessels were produced, in contrast, administration of wild-type VEGF in the fibrin glue lead to generation of leaky, disorganized blood vessels (Ehrbar, et al. 2004. et al. *Circ Res* 94:1124-1132, which is incorporated by reference herein in its entirety).

Accordingly, given the notion that certain cell types possess the increasing ability to induce angiogenesis, investigators have begun trials administering a variety of cells in areas of hypoxia with the intention of stimulating angiogenesis through more physiological means. One of the original reports of such cellular angiogenesis therapy utilized 5 patients with advanced ischemic heart disease undergoing coronary artery bypass grafting. Autologous bone marrow mononuclear cells were collected from the iliac bone, purified by apheresis, were adjusted to concentrations of $5-10\times 10^8$ cells per ml and injected into the ungraftable area of the myocardium at an injection volume of 0.1 ml ($5-10\times 10^7$ cells per injection). Injections were spaced 1 cm apart, and performed using a 1 ml syringe and a 26-gauge needle. The number of injections ranged from 5-22, with total cells injected ranging from $5-10\times 10^8$. 1 month and 1 year after the intervention, angiographic and radionuclide imagining demonstrating collateral vessel formation in the areas of injection in 3 of the 5 patients (Hamano, et al. 2001. *Jpn Circ J* 65:845-847, which is incorporated by reference herein in its entirety). Although this study had only 5 patients, and improvement was observed in only a subset, it does demonstrate the feasibility and safety of administering bone marrow into a highly sensitive area of the human body. Additionally, the fact that up to 22 injections can be performed without adverse effects supports the use of such cellular therapy in less invasive conditions associated with hypoperfusion.

Another study of a similar nature was conducted with 14 patients with one or more areas of transmural myocardial infarction. Given that during bypass surgery the sternum is removed to facilitate interventional procedures, this study actually withdrew marrow from this source. Patient marrow was diluted in autologous serum at a ratio of 1:2, and then injected 1 cm apart into the mid-depth of the left ventricular scar. In post-injection follow-up no serious adverse events were observed. Interestingly, stress echocardiography demonstrated overall improvement in the global and regional left ventricular function 6 weeks and 10 months after CABG. Specifically, of 34 infarcted left ventricular segments, 11 were injected with bone marrow alone, 13 were revascularized with a bypass graft alone, and 10 received bone marrow transplantation and a bypass graft in combination. Only the left ventricle segmental wall motion score of the areas injected with bone marrow and receiving a bypass graft in combination improved at dobutamine stress (Galinanes, et al. 2004. *Cell Transplant* 13:7-13, which is incorporated by reference herein in its entirety). This study demonstrated not only safety, but also localized functional effects of the cellular injection. Unfortunately, the study did not conclusively demonstrate that the benefit attained was due solely to angiogenesis induction but could also have been attributed to transdifferentiation of bone marrow cells to myocardial tissue (Orlic, et al. 2001. *Proc Natl Acad Sci USA* 98:10344-10349, which is incorporated by reference herein in its entirety). Although there is controversy as to whether bone marrow stem cells can actually transdifferentiate (Murry, et al. 2004. *Nature* 428:664-668; Balsam, et al. 2004. *Nature* 428:668-673, each of which is incorporated by reference herein in its entirety), the recent demonstration that intraembryonic injection of bone marrow into myocardial areas leads to transdifferentiation, at least conceptually, suggests that transdifferentiation is possible (Eisenberg, et al. 2006. *Stem Cells*, which is incorporated by reference herein in its entirety). For the purposes of the invention disclosed herein, it is irrelevant whether stem cells themselves undergo transdifferentiation into endothelium, as some has suggested, or whether stem cells provide trophic factors and support for resident endothelium and endothelial precursors to produce angiogenesis. What is relevant is the notion that numerous preclinical and clinical studies have demonstrated, including in randomized trials, that stem cells are associated with induction of angiogenesis.

Direct evaluation of angiogenesis in the myocardial setting can only be observed through perfusion analysis using radionuclide imaging. In a study of 10 patients undergoing off-pump coronary artery bypass surgery that were injected with autologous bone marrow mononuclear cells ($3.4+/-1.2\times 10^9$: which had $5.2+/-1.6\times 10^6$ CD34-positive cells) into ungraftable areas, a observation of myocardial (99m)Tc tracer uptake on the dipyridamole-stress image increased similarly in BMCT- and OPCAB-treated areas, whereas tracer accumulation at rest did not change in all myocardial areas. Interestingly, while the improvement of myocardial perfusion was not correlated with the total number of mononuclear cells transplanted, it was positively correlated with the number of transplanted CD34(+) cells. This is in agreement with the notion that the angiogenic component of bone marrow resides in the CD34+ fraction. Angiogenesis was further demonstrated in myocardial histopathology in 2 of 3 autopsy cases of patients who had died of unrelated causes (Yaoita, et al. 2005. *J Nucl Med* 46:1610-1617, which is incorporated by reference herein in its entirety).

Therapeutic angiogenesis using cell therapy was also performed clinically in the context of CLI. In one report, 2 studies were performed injecting autologous bone marrow mononuclear cells in patients with CLI, including rest pain, non-healing ischaemic ulcers, or both, who were not eligible for nonsurgical or surgical revascularisation. Haemodynamic inclusion criteria included resting ankle-brachial pressure index (ABI) less than 0·6 in the affected limb on two consecutive examinations done at least 1 week apart. Patients with poorly controlled diabetes mellitus (HbAlc>6·5% and proliferative retinopathy) or with evidence of malignant disorder during the past 5 years were excluded. 500 ml of bone marrow aspirate was extracted from the ileum, and gathered into plastic bags containing heparin. Mononuclear cells were selected using a CS3000-Plus blood-cell separator to 95% purity and concentrate to a final volume of about 30 mL. Cells were implanted about 3 h after marrow aspiration by intramuscular injection into the gastrocnemius of ischaemic legs. Approximately $2\times 10^9$ cells in a volume of 30 mL, were injected in total. Specifically, 0.75 mL of bone marrow-mononuclear cells were injected per site, with a total of 40 injections administered using a 3×3 cm grid and 26-gauge needle, to the depth of 1.5 cm. In the first study, 25 patients were injected with the bone marrow cells alone. In the second study 20 patients were injected with bone marrow cells in one of the ischemic limbs, whereas control mononuclear cells were injected into the other ischemic limb. In both groups a significant increase in treadmill walking time, ankle brachial index, and transcutaneous oxygen (TcO2) was observed, while in control, PBMC injected limbs no improvement was seen. Improvement was observed at 4 weeks post treatment and maintained for 24 weeks (Tateishi-Yuyama, et al. 2002. *Lancet* 360:427-435, which is incorporated by reference herein in its entirety).

In a Polish study, 10 Fontaine IV CLI patients were treated with autologous bone marrow mononuclear cells via intramuscular injection In the majority of patients, an improvement of the peripheral blood flow assessed by Laser Doppler Flux and percutaneous oxygen partial pressure was found as well as decrease in pain severity (Nizankowski, et al. 2005. *Kardiol Pol* 63:351-360; discussion 361, which is incorporated by reference herein in its entirety). No treatment associated adverse events were reported.

In another study, 7 CLI patients were treated with $1.6 \times 10^9$ autologous bone marrow cells by intramuscular injection. The leg blood flow (LBF) response to acetylcholine was increased subsequent to cellular therapy, as well, improvement in ABI, TcO2, and pain-free walking time was observed. This study suggests that angiogenesis induced by cellular therapy gives rise not only to increased perfusion, but also to enhanced biological activity (Higashi, et al. 2004. *Circulation* 109:1215-1218, which is incorporated by reference herein in its entirety).

Anti-Inflammatory Properties of Stem Cells: Bone Marrow Natural Suppressor Cells Numerous physiological safeguards are in place to protect sensitive organs from unwanted inflammatory activities. For example the ocular system contains high concentrations of FasL and TGF-b in the anterior chamber and associated structures to induce apoptosis/inhibition of activated T cells which may otherwise cause visual distortion through local inflammation (Kezuka, et al. 2000. *Immunology* 99:451-457; Yamamoto, et al. 2005. *Ophthalmic Res* 37:29-33, each of which is incorporated by reference herein in its entirety). Similar mechanisms exist to protect the testis (Aoki, et al. 2001. *Nat Immunol* 2:333-337, which is incorporated by reference herein in its entirety), central nervous system (Choi, et al. 2004. *Brain Res Brain Res Rev* 44:65-81, which is incorporated by reference herein in its entirety), and placenta (Niederkorn, et al. 2005. *Transplantation* 80:1139-1144, which is incorporated by reference herein in its entirety). In the bone marrow, due to the exquisite sensitivity of bematopoietic cells to inflammatory stimuli such as TNF or IFN-g (Bloom, et al. 2004. *Exp Hematol* 32:1163-1172; Tong, J., et al. 1991. *Exp Hematol* 19:312-316; Miura, et al. 1991. *Br J Haematol* 78:442-449, each of which is incorporated by reference herein in its entirety), a variety of anti-inflammatory activities are known to exist. For example, the bone marrow CD34+ stem cell population is known to express FasL (Brazil, et al. 2002. *Blood Cells Mol Dis* 29:94-103, which is incorporated by reference herein in its entirety) which is involved not only in causing apoptosis of activated T cells, but also selectively killing Th1 cells which have enhanced pro-inflammatory activity, thereby and providing an immune privileged environment. The importance of the immunomodulatory effects of FasL on CD34 cells is demonstrated in experiments where bone marrow induced allo-transplant tolerance is dependent on functional expression of FasL on the donor cells (George, et al. 1998. *Nat Med* 4:333-335, which is incorporated by reference herein in its entirety). In addition to surface-bound immune suppressive molecules, bone marrow contains a myeloid cell population, originally termed "natural suppressor cells" which inhibit immune activation in an antigen non-specific manner. Initial evidence of this suppressive population was seen when whole bone marrow cells were used as stimulators of the mixed lymphocyte reaction. The low-density bone marrow fraction was associated not only with poor allostimulatory ability, but also was capable of inhibiting on-going mixed lymphocyte reactions (Singhal, et al. 1970. *J Exp Med* 131:149-164; Adler, et al. 1976. *Adv Exp Med Biol* 66:599-605, each of which is incorporated by reference herein in its entirety). Numerous soluble factors have been described as responsible for immune suppressive activity such as nitric oxide, TGF-b, and a low molecular weight non-protein entity described as reptimed (DeKoter, et al. 1997. *Cell Immunol* 175:120-127, which is incorporated by reference herein in its entirety). Molecular characterization of cells with a "natural suppressor" phenotype revealed these cells to be equivalent to a myeloid progenitor during differentiation. Specific phenotypic markers identified to date include CD33, CD34, IL-3 receptor associated protein, and a high adherence to wheat germ agglutinin (Sugiura, et al. 1998. *Stem Cells* 16:99-106; Sugiura, et al. 1992. *Exp Hematol* 20:256-263, each of which is incorporated by reference herein in its entirety). Given that these natural suppressor cells are biologically identical to myeloid progenitor cells and also share properties with immature myeloid dendritic cells, we will include these cells within the definition of "stem cell" for the purposes of describing the invention disclosed herein.

Anti-Inflammatory Properties of Stem Cells: Mesenchymal Stem Cells

Another component of the bone marrow that contains anti-inflammatory activity is the mesenchymal stem cell. This cell population is the subject of U.S. Pat. No. 5,486,359, which is incorporated by reference herein in its entirety, which identifies mesenchymal stem cells as "formative pluripotential blast cells found inter alia in bone marrow, blood, dermis and periosteum that are capable of differentiating into any of the specific types of mesenchymal or connective tissues (i.e. the tissues of the body that support the specialized elements; particularly adipose, osseous, cartilaginous, elastic, and fibrous connective tissues) depending upon various influences from bioactive factors, such as cytokines". Specifically, mesenchymal stem cells are routinely described in the literature as being easily purified from bone marrow by positive selection of cells for markers such as LFA-3, ICAM-1, PECAM-1, P-selectin, L-selectin, CD49b/CD29, CD49c/CD29, CD49d/CD29, CD61, CD18, CD29, 6-19, thrombomodulin, CD10, CD13, STRO-1, STRO-2, VCAM-1, CD146, THY-1, or by negative selection for markers associated with hematopoietic cells such as the CD45 antigen. Alternatively, mesenchymal cells can be generated by culture of bone marrow in various culture media and collection of the adherent cell population. This expansion technique is sometimes using in combination with selection procedures for markers described above to generate a pure population of stem cells. Alternatively, it is known that mesenchymal stem cells may be generated from embryonic stem cells using feeder-free cultures, thus allowing for clinical utility without fear of murine feeder cell contamination (Olivier, et al. 2006. *Stem Cells*, which is incorporated by reference herein in its entirety).

Mesenchymal stem cells are known to constitutively secrete immune inhibitory factors such as IL-10 and TGF-b while maintaining ability to present antigens to T cells (Liu, et al. 2004. *Transplant Proc* 36:3272-3275; Togel, et al. 2005. *Am J Physiol Renal Physiol* 289:F31-42, each of which is incorporated by reference herein in its entirety). This is believed to further allow inhibition of immunity in an antigen specific manner, as well as to allow the use of such cells in an allogeneic fashion without fear of immune-mediated rejection. Further understanding of the immune inhibitory effects of mesenchymal stem cells comes from the fact that during T cell activation, two general signals are required for the T cell in order to mount a productive immune response, the first signal is recognition of antigen, and the second is recognition of costimulatory or coinhibitory signals. Mesenchymal cells present antigens to T cells but provide a coinhibitory signal instead of a co-stimulatory signal, thus specifically inhibiting T cells that recognize them, and other cells expressing similar antigens. Supporting this concept, it was demonstrated in a murine model that flk-1+Sca-1-mesenchymal stem cell transplantation leads to permanent donor-specific immunotolerance in allogeneic hosts and results in long-term allogeneic skin graft acceptance (Deng, et al. 2004. *Exp Hematol* 32:861-867, which is incorporated by reference herein in its entirety). Other studies have shown that mesenchymal stem cells are inherently immunosuppressive through production of PGE-2, interleukin-10 and expression of the tryptophan catabolizing enzyme indoleamine 2,3,-dioxygenase as well as Galectin-1 (Kadri, et al. 2005. *Stem Cells Dev* 14:204-212; Ryan, et al. 2005. *J Inflamm (Lond)* 2:8, each of which is incorporated by reference herein in its entirety). These stem cells also have the ability to non-specifically modulate the immune response through the suppression of dendritic cell maturation and antigen presenting abilities (Beyth, et al. 2005. *Blood* 105:2214-2219; Aggarwal, et al. 2005. *Blood* 105: 1815-1822, each of which is incorporated by reference herein in its entirety). Immune suppressive activity is not dependent on prolonged culture of mesenchymal stem cells since functional induction of allogeneic T cell apoptosis was also demonstrated using freshly isolated, irradiated, mesenchymal stem cells (Plumas, et al. 2005. *Leukemia* 19:1597-1604, which is incorporated by reference herein in its entirety). Others have also demonstrated that mesenchymal stem cells have the ability to preferentially induce expansion of antigen specific T regulatory cells with the CD4+ CD25+ phenotype (Maccario, et al. 2005. *Haematologica* 90:516-525, which is incorporated by reference herein in its entirety). Supporting the potential clinical utility of such cells, it was previously demonstrated that administration of mesenchymal stem cells inhibits antigen specific T cell responses in the murine model of multiple sclerosis, experimental autoimmune encephalomyelitis, leading to prevention and/or regression of pathology (Zappia, et al. 2005. *Blood* 106:1755-1761, which is incorporated by reference herein in its entirety). Safety of infusing mesenchymal stem cells was illustrated in studies administering $1-2.2\times10^6$ cells/kg in order to enhance engraftment of autologous bone marrow cell. No adverse events were associated with infusion, although level of engraftment remained to be analyzed in randomized trials (Koc, et al. 2000. *J Clin Oncol* 18:307-316, which is incorporated by reference herein in its entirety).

In a matched pair analysis study, it was demonstrated that in vitro expanded mesenchymal stem cells reduced both acute and chronic graft versus host disease in the allogeneic bone marrow transplant setting. Clinical administration of mesenchymal stem cells was reported in a patient suffering severe, grade IV graft versus host disease in the liver and gut subsequent to bone marrow transplant. Administration of $2\times10^6$ cells/kg on day 73 after bone marrow transplant lead to a long term remission of graft versus host disease, which was maintained at the time of publication, 1 year subsequent to administration of the mesenchymal stem cells (Le Blanc, et al. 2004. *Lancet* 363:1439-1441, which is incorporated by reference herein in its entirety). A feasibility study in 46 patients receiving mesenchymal cells prior to transplant revealed a favorable safety profile and is encouraging further dose finding studies (Lazarus, et al. 2005. *Biol Blood Marrow Transplant* 11:389-398, which is incorporated by reference herein in its entirety).

Although, as stated above, mesenchymal stem cells are classically obtained from bone marrow sources for clinical use this source may have disadvantages because of the invasiveness of the donation procedure and the reported decline in number during aging. Alternative sources of mesenchymal stem cells include adipose tissue (Knippenberg, et al. 2005. *Tissue Eng* 11:1780-1788, which is incorporated by reference herein in its entirety), placenta (Portmann-Lanz, et al. 2006. *Am J Obstet Gynecol* 194:664-673; Zhang, et al. 2006. *Biochem Biophys Res Commun* 340:944-952, each of which is incorporated by reference herein in its entirety), scalp tissue (Shih, et al. 2005. *Stem Cells* 23:1012-1020, which is incorporated by reference herein in its entirety) and cord blood (Kadivar, et al. 2006. *Biochem Biophys Res Commun* 340:639-647, which is incorporated by reference herein in its entirety). A recent study compared mesenchymal stem cells from bone marrow, cord blood and adipose tissue in terms of colony formation activity, expansion potential and immunophenotype. It was demonstrated that all three sources produced mesenchymal stem cells with similar morphology and phenotype. Ability to induce colony formation was highest using stem cells from adipose tissue and interestingly in contrast to bone marrow and adipose derived mesenchymal cells, only the cord blood derived cells lacked ability to undergo adipocyte differentiation; Proliferative potential was the highest with cord blood mesenchymal stem cells which were capable of expansion to approximately 20 times, whereas cord blood cells expanded an average of 8 times and bone marrow derived cells expanded 5 times (Kern, et al. 2006. *Stem Cells*, which is incorporated by reference herein in its entirety).

The current art teaches a variety of methods for treatment of lower back pain, unfortunately, none of the methods that are clinically applicable actually prevent the process of disc degeneration. Early intervention methods such as exercise, antiinflammatories or analgesics do not influence the root cause of the problem. Later interventions such as spinal fusion, surgery, or artificial disc implants are burdened with adverse effect, invasiveness and limited full recovery. Methods under development for treatment of the disc degeneration process, such as intra-discal stem cell therapy, as disclosed in U.S. Pat. Application No. 20060018887 or No. 20050154463, each of which is incorporated by reference herein in its entirety, are far from clinical implementation. Additionally, published data on intra-discal administration of stem cells has not demonstrated therapeutic efficacy but were only correlative (Sakai, et al. 2005. *Spine* 30:2379-2387, which is incorporated by reference herein in its entirety). In light of this, novel methods and approaches are needed for addressing the problem of lumbar pain in a regenerative manner. The invention disclosed herein teaches such methods and compositions of matters useful in their practice.

It is within the scope of this invention to teach novel methods of treating or substantially ameliorating lower back pain through administration of cells capable of stimulating angiogenesis. Such embodiments are disclosed in U.S. Provisional Application Ser. No. 60/801,957, filed May 19, 2006 which is incorporated herein by reference in its entirety. Although some embodiments are described below, these are merely representative and one of skill in the art will be able to extrapolate numerous other applications and deviates that are still within the scope of the invention disclosed.

In one embodiment, patients with advanced lumbar back pain are screened to determine whether the pain is associated with disc degeneration. Said screening is common medical practice and includes techniques such as physical examination, radiographic studies, MRI and bone scan. Diagnosis of "discogenic" pain, or pain associated with degeneration of the annulus fibrosis, nerve irritation by the nucleus pulposus, or other chronic pain. Patients with osteoporosis, spinal infections or tumors, acute nerve compression and arthritis are excluded from eligibility for treatment using the methods and compositions described in the present invention. In a variety of cases, patients treated with the invention disclosed will be refractory to conventional treatments such as anti-inflammatories or analgesics.

Patients suitable for intervention undergo a bone marrow harvest with the goal of acquiring approximately 5-700 ml of bone marrow aspirate. Numerous techniques for the aspiration of marrow are described in the art and part of standard medical practice. One particular methodology that may be attractive due to decreased invasiveness is the "mini-bone marrow harvest" (Mineishi, S. 2003. *Nippon Rinsho* 61:1489-1494, which is incorporated by reference herein in its entirety). Said aspirate is used as a starting material for purification of cells with angiogenic activity. In one specific embodiment bone marrow mononuclear cells are isolated by pheresis or gradient centrifugation. Numerous methods of separating mononuclear cells from bone marrow are known in the art and include density gradients such as Ficoll Histopaque at a density of approximately 1.077 g/ml or Percoll gradient. Separation of cells by density gradients is usually performed by centrifugation at approximately 450 g for approximately 25-60 minutes. Cells may subsequently be washed to remove debris and unwanted materials. Said washing step may be performed in phosphate buffered saline at physiological pH. An alternative method for purification of mononuclear cells involves the use of apheresis apparatus such as the CS300-Plus blood-cell separator (Baxter, Deerfield, USA), the Haemonetics separator (Braintree, Mass.), or the Fresenius AS 104 and the Fresenius AS TEC 104 (Fresenius, Bad Homburg, Germany) separators. In general, apheresis is used to isolate cellular components from the blood and involves removing blood from a subject, subjecting the blood to a separation method to remove certain components, and reinfusing the blood into the subject in a continuous manner.

In one embodiment of the invention bone marrow mononuclear cells are concentrated in an injection solution, which can be saline, mixtures of autologous plasma together with saline, or various concentrations of albumin with saline. A preferred pH of the injection solution is from about 6.4 to about 8.3, optimally about 7.4. Excipients can be used to bring the solution to isotonicity such as, 4.5% mannitol or 0.9% sodium chloride, pH buffers with art-known buffer solutions, such as sodium phosphate. Other pharmaceutically acceptable agents can also be used to bring the solution to isotonicity, including, but not limited to, dextrose, boric acid, sodium tartrate, propylene glycol, polyols (such as mannitol and sorbitol) or other inorganic or organic solutes.

Cells can be concentrated into a volume of 5-40 ml, or more preferably in a volume of 10-15 ml at a concentration of $1-10 \times 10^8$ cells/ml. Administration into the patient is performed in an area proximal to the disc in need of therapy. Alternatively, injection of cells can be performed in an area proximal to occluded vessels that feed the lumbar area associated with pain. Numerous methods are known in the art to identify the disc segment causative of lower back pain, as well as areas of hypoperfusion. These include diffusion-weighted imaging, magnetic resonance imaging, diffusion tensor imaging, magnetic resonance spectroscopy, functional magnetic resonance imaging, dynamic computed tomography and magnetic resonance imaging, T2 relaxometry MRI, CT-scan, and provocative discography (Haughton, V. 2006. *J Bone Joint Surg Am* 88 Suppl 2:15-20, which is incorporated by reference herein in its entirety).

In one particular embodiment, the area of hypoperfusion is identified using technetium-99m Sestamibi in conjunction with single photon emission computed tomography (SPECT) imaging. This radiolabelled lipophilic cation is injected intravenously at concentrations ranging from 200-1790 MBq, more preferably 500-1000 MBq, and even more preferable at approximately 750 MBq. Imaging is performed with a gamma camera and absorption/perfusion is quantified using various softwares known to one skilled in the art.

Determination of injection site takes into account a variety of patient-specific variables. In one embodiment cells are injected into the paraspinalis muscles using a needle of sufficient gauge to enter the muscular area at least one centimeter without causing said patient substantial pain. Injections are made multiple, repeating manners with an average number of 1-30 injections, more preferably, 5-15. In other embodiments cells are administered under ultrasound-guidance to muscles such as the psoas major.

One of the guiding principles behind practice of the invention is the notion that poor perfusion is a causative and/or maintenance factor in the propagation of lower back pain. Accordingly, in some embodiments of the invention, administration of bone marrow cells is performed in proximity to lumbar and/or medial sacral arteries. The observation that atherosclerotic occlusion of these arteries is present in the majority of patients with intractable lower back pain suggests that injection of angiogenesis promoting bone marrow stem cells can be performed, within the context of this invention, into areas proximal to said lumbar and/or medial sacral arteries.

Subsequent to administration of bone marrow cells, observation of lumbar circulation and/or perfusion can be performed in order to quantify angiogenic effects. Methods of observing perfusion include but are not limited to angiography, radionuclide imaging, magnetic resonance imaging, doppler ultrasound, and the like. Concurrently pain measurements such as the Visual Analogue Score, or disability assessments such as the Owestry Disability Index, can be used to quantify extent of therapeutic benefit. The need for subsequent administration of cells can be tailored around the level of response observed.

Based on the spirit of this invention, that administration of cells with angiogenic capability are useful for the treatment of certain types lower back pain, it will be obvious to one skilled in the art that numerous variation can be made to increase efficacy of the therapy thought herein. For example, while bone marrow cells themselves can be directly injected intramuscularly, as described above, purified population of bone marrow cells can also be utilized. It is known that AC133+ bone marrow cells are enriched for angiogenic stimulatory capacity in comparison to whole bone marrow mononuclear cells (Pompilio, et al. 2004. *Ann Thorac Surg* 78:1808-1812; Hilbe, et al. 2004. *J Clin Pathol* 57:965-969, each of which is incorporated by reference herein in its entirety). Accordingly this subpopulation can be purified from bone marrow through the use of techniques widely available to one skilled in the art. Suitable techniques include, but are not limited to, paramagnetic isolation methods such as magnetic activated cell sorting (MACS), isolation methods based on fluorescent labeling such as fluorescent activated cell sorting (FACS), immunoaffinity methods, and the like. Other subpopulations of bone marrow cells can also be enriched in order to enhance angiogenic ability, these include but are not limited to cells with expression of markers such as CD34, VEGFR-2, flt-1, and the like.

In one embodiment of the invention bone marrow cells can be cultured ex vivo in order to expand cell numbers such that the amount of marrow needed to be harvested remains minimized. Methods of expansion can be selected to increase the numbers and/or activity of cells with angiogenic ability such as CD34+ cells. Said methods include culturing with various cocktails of growth factors including, insulin-like growth factor (IGF), epidermal growth factor (EGF), transforming growth factor beta (TGF-beta), acidic and basic fibroblast growth factor (FGF-1 and FGF-2), FGF-4, or other members of this family, activin A, a bone morphogenetic protein (BMP), PDGF, insulin, erythropoietin, members of the platelet-derived growth factor (PDGF) family, including PDGF-AB, PDGF-BB and PDGF-AA; EGFs, members of the insulin-like growth factor (IGF) family, including IGF-I and -II, angiogenin(s), endothelins, hepatocyte growth factor, placental growth factor, keratinocyte growth factor; HBGF-1 and HBGF-2; growth differentiation factors (GDFs), members of the hedgehog family of proteins, including indian, sonic and desert hedgehog; ADMP-1; GDF-5; and members of the colony-stimulating factor (CSF) family, including CSF-1, G-CSF, and GM-CSF; and isoforms thereof. The growth factor can also be derived from cell products such as platelet rich plasma or supernatant of cultured cells, including supernatant of cells cultured under hypoxic conditions.

In terms of specific concentrations of growth factors to be used in expanding stem cells and, according to the invention herein, stem cells with angiogenic potential, the practitioner of the invention is referred to the following references for examples, each of which is incorporated by reference herein in its entirety: TPO (Wang, et al. 2005. *Ann N Y Acad Sci* 1044:29-40; Xie, et al. 2003. *Blood* 101:1329-1335; Feugier, et al. 2002. *J Hematother Stem Cell Res* 11:127-138; Kawada, et al. 1999. *Exp Hematol* 27:904-915; Won, et al. 2000. *J Hematother Stem Cell Res* 9:465-473), SCF (Wang, et al. 2005. *Cell Biol Int* 29:654-661; Levac, et al. 2005. *Haematologica* 90:166-172; Peschle, et al. 1993. *Stem Cells* 11:356-370), IL-1 (Maurer, et al. 2000. *Int J Hematol* 71:203-210; Willems, et al. 2001. *Ann Hematol* 80:17-25; Scheding, et al. 2000. *Exp Hematol* 28:460-470), IL-3 (Ivanovic, Z. 2004. *Eur Cytokine Netw* 15:6-13; Inderbitzin, et al. 2005. *J Gastrointest Surg* 9:69-74; Bohmer, R. M. 2004. *Stem Cells* 22:216-224), IL-6 (Quesenberry, et al. 1991. *J Cell Biochem* 45:273-278; Zhang, et al. 2005. *Mol Cell Neurosci*.; Taga, et al. 2005. *Clin Rev Allergy Immunol* 28:249-256; Nakamura, et al. *Clin Rev Allergy Immunol* 28:197-204), IL-7 (Ficara, et al. 2004. *Mol Ther* 10:1096-1108; Krawczenko, et al. 2005. *Arch Immunol Ther Exp (Warsz)* 53:518-525; Andre-Schmutz, et al. 2004. *Br J Haematol* 126:844-851; De Waele, et al. 2004. *Eur J Haematol* 72:193-202), IL-11 (Willems et al., supra; Lu, et al. 2003. *Zhonghua Xue Ye Xue Za Zhi* 24:589-592; Momose, et al. 2002. *Arzneimittelforschung* 52:857-861; Van der Meeren, et al. 2002. *Radiat Res* 157:642-649), flt-3L (Li, et al. 2005. *Eur J Haematol* 74:128-135; McGuckin, et al. 2004. *Cell Prolif* 37:295-306; Lu, et al. 2004. *Blood* 103:4134-4141; Streeter, et al. 2003. *Exp Hematol* 31:1119-1125), G-CSF (Aliotta, et al. 2006. *Exp Hematol* 34:230-241; Jung, et al. 2006. *Brain Res*.; Kogler, et al. 2005. *Exp Hematol* 33:573-583), GM-CSF (Quesenberry et al., supra; Gangenahalli, et al. 2005. *Stem Cells Dev* 14:140-152), Epo Otani, et al. 2004. *Exp Hematol* 32:607-613; Yao, et al. 2000. *Bone Marrow Transplant* 26:497-503; Mobest, et al. 1998. *Biotechnol Bioeng* 60:341-347), FGF-1 (Crcareva, et al. 2005. *Exp Hematol* 33:1459-1469; de Haan, et al. 2003. *Dev Cell* 4:241-251), FGF-2 (Ratajczak, et al. 1996. *Br J Haematol* 93:772-782; Kang, et al. 2005. *Stem Cells Dev* 14:395-401), FGF-4 (Schwartz, et al. 2005. *Stem Cells Dev* 14:643-655; Quito, et al. 1996. *Blood* 87:1282-1291), FGF-20 (Grothe, et al. 2004. *Neurobiol Dis* 17:163-170), IGF (McDevitt, et al. 2005. *J Mol Cell Cardiol* 39:865-873; Musaro, A. 2005. *Arch Ital Biol* 143:243-248; Zumkeller, et al. 1999. *Blood* 94:3653-3657; Okajima, et al. 1998. *J Biol Chem* 273:22877-22883), EGF (Miyazaki, et al. 2004. *Cell Transplant* 13:385-391; von Ruden, et al. 1988. *Embo J* 7:2749-2756), NGF (Bracci-Laudiero, et al. 2003. *J Neuroimmunol* 136:130-139; Simone, et al. 1999. *Hematol Oncol* 17:1-10), LIF (Guo, et al. 2005. *Stem Cells*; Chodorowska, et al. 2004. *Ann Univ Mariae Curie Sklodowska [Med]* 59:189-193), PDGF (Su, et al. 2005. *Stem Cells Dev* 14:223-230; Lucarelli, et al. 2003. *Biomaterials* 24:3095-3100; Yang, et al. 1995. *Br J Haematol* 91:285-289), BMPs (Ploemacher, et al. 1999. *Leukemia* 13:428-437; Zhang, et al. 2005. *Dev Biol* 284:1-11; Jay, et al. 2004. *Cell Res* 14:268-282; Chadwick, et al. 2003. *Blood* 102:906-915; Dormady, et al. 2001. *J Hematother Stem Cell Res* 10:125-140), activin-A (Shav-Tal, et al. 2002. *Stem Cells* 20:493-500), VEGF (Cerdan, et al. 2004. *Blood* 103:2504-2512), forskolin (Laharrague, et al. 1998. *Faseb J* 12:747-752; Gaspar Elsas, et al. 2000. *Br J Pharmacol* 130:1362-1368), and glucocorticoids (Grafte-Faure, et al. 1999. *Am J Hematol* 62:65-73).

In one embodiment cells are cultured in the presence of growth factors with a media composition capable of sustaining cellular viability ex vivo. Such media compositions are widely known in the art and include, for example, Iscove's modified Dulbecco's Media (IMDM) media, DMEM, KO-DMEM, DMEM/F12, RPMI 1640 medium, McCoy's 5A medium, minimum essential medium alpha medium (alpha.-MEM), F-12K nutrient mixture medium (Kaighn's modification, F-12K), X-vivo 20, Stemline, CC100, H2000, Stemspan, MCDB 131 Medium, Basal Media Eagle (BME), Glasgow Minimum Essential Media, Modified Eagle Medium (MEM), Opti-MEM I Reduced Serum Media, Waymouth's MB 752/1 Media, Williams Media E, Medium NCTC-109, neuroplasma medium, BGJb Medium, Brinster's BMOC-3 Medium, CMRL Medium, CO2-Independent Medium, and Leibovitz's L-15 Media. Culturing of said cells can be performed in the presence of autologous serum, or using serum-free composition or serum-substituting cocktails. For example, a serum substitute such as commercially available mixtures can be used including, but not limited to BIT9500 (Stem Cell Technologies, Vancouver Canada), X-VIVO-10 or X-VIVO-15 (Cambrex BioSciences, Baltimore, USA) or AIM-V media (InVitrogen, Carlsbad, USA). In other embodiments, the serum substitute is comprised of bovine serum albumin (BSA), insulin, and transferrin (TF). Alternatively, human serum albumin USP can be used. The serum substitute can be comprised of about 0.1 to about 0.50 g/liter of human serum albumin, about 0.01 to about 1000 µg/ml insulin, and about 0.1 to about 1000 µg/ml transferrin. In another more preferred embodiment the serum substitute can be comprised of 4 g/liter of human serum albumin, 0.71 µg/ml of insulin and 27 µg/ml of transferrin. One of skill in the art will understand that depending on the angiogenesis promoting conditions desired, various concentrations and or substitution of components can be experimentally assessed and tailored according to the biological response sought. Output systems for determining angiogenic potency of stem cells can include expression of surface markers associated with cells bearing angiogenic potential, but can also include biological assays such as ability to induce neovasculature in immunodeficient animals subjected to ischemia. Currently used models include the hind-limb ischemia system described in the following references (Heeschen, et al. 2004. *Circulation* 109:1615-1622; Akita, et al. 2003. *Lab Invest* 83:65-73, each of which is incorporated by reference herein in its entirety). Other methods of characterizing angiogenic potency include the ability of cells to home to chemotactic gradients generated by hypoxic tissue. In vitro assays include assessment of homing towards a SDF-1 or VEGF gradient (Heeschen et al., supra).

Given the above-mentioned methods of assessing angiogenic capability of a cellular population, numerous methods can be used to endow/enhance angiogenic capabilities of the starting bone marrow population. In one embodiment mesenchymal cells are generated through culture. For example, U.S. Pat. No. 5,486,359, which is incorporated by reference herein in its entirety, describes methods for culturing such and expanding mesenchymal stem cells, as well as providing antibodies for use in detection and isolation. U.S. Pat. No. 5,942,225, which is incorporated by reference herein in its entirety, teaches culture techniques and additives for differentiation of such stem cells which can be used in the context of the present invention to produce increased numbers of cells with angiogenic capability. Although U.S. Pat. No. 6,387,369, which is incorporated by reference herein in its entirety, teaches the use of mesenchymal stem cells for regeneration of cardiac tissue, we believe that in accordance with published literature (Caplan, et al. 2006. *J Cell Biochem.*; Shyu, et al. 2006. *J Biomed Sci* 13:47-58, each of which is incorporated by reference herein in its entirety) stem cells generated through these means are actually angiogenically potent and therefore can be utilized in the context of the current invention for treatment/amelioration of lower back pain. Without being bound to a specific theory or mechanism of action, it appears that mesenchymal stem cells induce angiogenesis through production of factors such as vascular endothelial growth factor, hepatocyte growth factor, adrenomedullin, and insulin-like growth factor-1 (Nagaya, et al. 2005. *Circulation* 112:1128-1135, which is incorporated by reference herein in its entirety).

Treatment of patients with lower back pain can be accomplished through another embodiment of the invention disclosed through the administration of cells that have been genetically modified to upregulate expression of angiogenic stimuli or anti-inflammatory activities. It is known in the art that genes can be introduced by a wide range of approaches including adenoviral, adeno-associated, retroviral, alpha-viral, lentiviral, Kunjin virus, or HSV vectors, liposomal, nano-particle mediated as well as electroporation and Sleeping Beauty transposons. Genes with angiogenic stimulatory function that can be transfected include but are not limited to: VEGF, FGF-1, FGF-2, FGF-4, EGF, and HGF. Additionally, transcription factors that are associated with upregulating expression of angiogenic cascades can also be transfected into cells used for treatment of lower back pain, said genes include but are not limited to: HIF-1α, HIF-2, NET, and NF-kB. Genes inhibitory to inflammation can be used such as: TGF-a, TGF-b, IL-4, IL-10, IL-13, IL-20, thrombospondin, and the like. Transfection can also be utilized for administration of genetic manipulation means in a manner to substantially block transcription or translation of genes which inhibit angiogenesis. Antisense oligonucleotides, ribozymes or short interfering RNA can be transfected into cells for use for treatment of lower back pain in order to block expression of antiangiogenic proteins such as: canstatin, IP-10, kringle 1-5, and collagen XVIII/endostatin. Additionally, said gene inhibitory technologies can be used for blocking ability of cells to be used for treatment of lower back pain to express inflammatory proteins including but not limited to: IL-1, TNF-α, IL-2, IL-6, IL-8, IL-9, IL-11, IL-12, IL-15, IL-17, IL-18, IL-21, IL-23, IL-27, IFN-α, IFN-β, IFN-γ, and the like. Globally acting transcription factors associated with inflammation can also be substantially blocked using not only the genetic means described but also decoy oligonucleotides. Suitable transcription factors for blocking include but are not limited to various subunits of the NF-kB complex such as p55, and/or p60, STAT family members, particularly STAT1, STAT5, STAT4, and members of the Interferon Regulatory Factor family such as IRF-1, IFR-3, IFR-8, and the like.

Enhancement of angiogenic stimulation ability of the cells useful for the treatment of back pain can be performed through culturing under conditions of restricted oxygen. It is known in the art that stem cells in general, and ones with angiogenesis promoting activity specifically, tend to reside in hypoxia niches of the bone marrow. When stem cells differentiate into more mature progeny, they progressively migrate to areas of the bone marrow with higher oxygen tension (Ivanovic, et al. 2002. *Exp Hematol* 30:67-73, which is incorporated by reference herein in its entirety). This important variable in tissue culture was used in studies that demonstrated superior expansion of human CD34 stem cells capable of full hematopoietic reconstitution were obtained in hypoxic conditions using oxygen tension as low as 1.5%. The potent expansion under hypoxia, which was 5.8-fold higher as compared to normal oxygen tension was attributed to hypoxia induction of HIF-1 dependent growth factors such as VEGF, which are potent angiogenic stimuli when released under controlled conditions (Danet, et al. 2003. *J Clin Invest* 112:126-135, which is incorporated by reference herein in its entirety). Accordingly, culture of cells to be used for treatment of back pain can be performed in conditions of oxygen ranging from 0.5% to 4%, more preferably 1%-3% and even more preferably from 1.5%-1.9%. Hypoxia culture is not limited towards lowering oxygen tension but can also include administration of molecules that inhibit oxygen uptake or compete with oxygen uptake during the tissue culture process. Additionally, in an embodiment of the invention, hypoxia is induced through induction of agents that cause the upregulation of the HIF-1 transcription factor.

Subsequent to various culture procedures, cells generated can be tested for angiogenic and/or anti-inflammatory activity before use in clinical conditions. Testing can be performed by various means known to one skilled in the art. In terms of assessing angiogenic potential said means include, but are not limited to: a) Ability to support endothelial cell proliferation in vitro using human umbilical vein endothelial cells or other endothelial populations. Assessment of proliferation can be performed using tritiated thymidine incorporation or by visually counted said proliferating endothelial cells. A viability dye such as MTT or other commercially available indicators can be used; b) Ability to support cord formation in subcutaneously implanted matrices. Said matrices, which can include Matrigel or fibrin gel, are loaded with cells generated as described above and implanted subcutaneously in an animal. The animal can be an immunodeficient mouse such as a SCID or nude mouse in order to negate immunological differences. Subsequent to implantation formation of endothelial cords can be assessed visually by microscopy. In order to distinguish cells stimulating angiogenesis versus host cells responding to said cells stimulating angiogenesis, a species-specific marker can be used; c) Ability to accelerate angiogenesis occurring in the embryonic chicken chorioallantoic membrane assay. Cells can be implanted directly, or via a matrix, into the chicken chorioallantoic membrane on embryonic day 9 and cultured for a period of approximately 2 days. Visualization of angiogenesis can be performed using in vivo microscopy; and d) Ability to stimulate neoangiogenesis in the hind limb ischemia model described above.

Assessment of the anti-inflammatory abilities of cells generated or isolated for potential clinical use can also be performed. Numerous methods are known in the art, for example they can include assessment of the putative anti-inflammatory cells to modulate immunological parameters in vitro. Putative anti-inflammatory cells can be co-cultured at various ratios with an immunological cell. The immunological cell can be stimulated with an activatory stimulus. The ability of the putative anti-inflammatory cell to inhibit, in a dose-dependent manner, production of inflammatory cytokines or to augment production of anti-inflammatory cytokines, can be used as an output system of assessing anti-inflammatory activity. Additional output parameters can include, for example: proliferation, cytotoxic activity, production of inflammatory mediators, and upregulation of surface markers associated with activation. Cytokines assessed can include but are not limited to: IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, TNF, IFN, RANKL and the like. Specific immunological cells can be freshly isolated or can be immortalized cell lines. The immunological cells can be, for example: T cells, B cells, monocytes, macrophages, neutrophils, eosinophils, basophils, dendritic cells, natural killer cells, natural killer T cells, γδ-T cells, and the like. The immunological stimuli can include an antibody, a ligand, a protein, or another cells. Examples including: crosslinking antibodies to T cell receptor, to costimulatory molecules such as CD28, to activation associated molecules such as CD69 or to receptors for stimulatory cytokines such as IL-2. Additional examples of inflammatory stimuli can include co-culture with allogeneic stimulator cells such as in mixed lymphocyte reactions, or may include stimulation with a non-specific activator such as a lectin. Specific lectins can include conconavalin-A, phytohemagluttinin, or wheat germ agglutinin. Other non-specific stimulators can be activators of the toll like receptor pathway such as lipopolysaccharide, CpG DNA motifs or bacterial membrane fractions.

The methods described in the above two paragraphs are shown only as examples that can be used to determine, before entry into clinical use, whether a cell population generated as described in the present invention is capable of producing the desired angiogenic stimulatory or anti-inflammatory effects. These examples are only provided as guides which one skilled in the art will improve upon using routine experimentation and searching of the literature.

For all embodiments of the invention disclosed herein, cells to be used for treatment of lower back pain can be cryopreserved for subsequent use, as well as for transportation. One skilled in the art knows numerous methods of cellular cryopreservation. Typically, cells are treated to a cryoprotection process, then stored frozen until needed. Once needed cells require specialized care for revival and washing to clear cryopreservative agents that can have detrimental effects on cellular function. Generally, cryopreservation involves aspects of three main concepts: 1) the cryoprotective agent, 2) the control of the freezing rate, and 3) the temperature at which the cells will be stored at. Cryoprotective agents are well known to one skilled in the are and can include but are not limited to dimethyl sulfoxide (DMSO), glycerol, polyvinylpyrrolidine, polyethylene glycol, albumin, dextran, sucrose, ethylene glycol, i-erythritol, D-ribitol, D-mannitol, D-sorbitol, i-inositol, D-lactose, or choline chloride as described in U.S. Pat. No. 6,461,645, which is incorporated by reference herein in its entirety). A method for cryopreservation of cells that is preferred by some skilled artisans is DMSO at a concentration not being immediately cytotoxic to cells, under conditions which allow it to freely permeate the cell whose freezing is desired and to protect intracellular organelles by combining with water and prevent cellular damage induced from ice crystal formation. Addition of plasma at concentrations between 20-25% by volume can augment the protective effect of DMSO. After addition of DMSO, cells should be kept at temperatures below 4° C., in order to prevent DMSO mediated damage. Methods of actually inducing the cells in a state of suspended animation involve utilization of various cooling protocols. While cell type, freezing reagent, and concentration of cells are important variables in determining methods of cooling, it is generally accepted that a controlled, steady rate of cooling is optimal. There are numerous devices and apparatuses known in the field that are capable of reducing temperatures of cells for optimal cryopreservations. One such apparatus is the Thermo Electro Cryomed Freezer™ manufactured by Thermo Electron Corporation. Cells can also be frozen in CryoCyte™ containers as made by Baxter. One example of cryopreservation is as follows: $2 \times 10^6$ CD34 cells/ml are isolated from cord blood using the Isolex System™ as per manufacturer's instructions (Baxter). Cells are incubated in DMEM media with 10% DMSO and 20% plasma. Cooling is performed at 1° Celsius/minute from 0° to −80° C. When cells are needed for use, they are thawed rapidly in a water bath maintained at 37° C. and chilled immediately upon thawing. Cells are rapidly washed, either a buffer solution, or a solution containing a growth factor. Purified cells can then be used for expansion if needed. A database of stored cell information (such as donor, cell origination types, cell markers, etc.) can also be prepared, if desired.

In another embodiment of the invention, the cells chosen for therapy are not only are capable of stimulating angiogenesis, but also possess anti-inflammatory activities. Certain subsets of bone marrow cells, either freshly isolated or obtained through culture activity, secrete factors as well as possess membrane bound molecules that are capable of inhibiting immunologically mediated inflammation. One such useful cell is broadly described as a low-density myeloid progenitor, or termed by others as "natural suppressor" cells (Sugiura et al. 1998, supra). These cells are on the one hand capable of contributing to angiogenesis (Young, M. R. 2004. *Int J Cancer* 109:516-524, which is incorporated by reference herein in its entirety), while on the other hand exert potent anti-inflammatory activity (Angulo et al., supra). In one embodiment of the invention, the natural suppressor cells are purified from bone marrow of patients in need of treatment through buoyancy means such as counterflow elutriation or Percoll density gradient to select for cells of density ranging between about 1.055-about 1.065 g/ml. The cells can be substantially enriched for anti-inflammatory activity by positive selection for CD33 and/or CD34, and/or wheat germ agglutinin binding. The cells can be expanded by culture with various cytokines and growth factors or can be used immediately after purification. In one embodiment, administration of said cells occurs in the paraspinalis muscles using a needle of sufficient gauge to enter the muscular area at least one centimeter without causing said patient substantial pain. Injections are made multiple, repeating manners with an average number of 1-30 injections, more preferably, 5-15. In other embodiments cells are administered under ultrasound-guidance to muscles such as the psoas major. Total cell numbers administered are of a sufficient quantity to induce a localized anti-inflammatory effect, while concurrently stimulating an angiogenic response in the areas of lumbar hypo-perfusion. The cell concentration can range from about $1\times10^6$ to about $1\times10^9$, more preferably about $1\times10^7$ to about $1\times10^8$, and even more preferably about $2\times10^7$ to about $1\times10^8$.

In another embodiment natural suppressor cells, and/or endothelial progenitor cells are mobilized through the administration of a growth factor capable of eliciting such effect. Clinically used growth factors capable of mobilizing bone marrow progenitors with natural suppressor and/or angiogenic activity include: G-CSF, GM-CSF, and M-CSF. Given the intrinsic capability of both natural suppressor cells and endothelial progenitors to home into areas of inflammation and/or hypoxia, such mobilization allows the redistribution of cells to areas where needed, without the need for external cellular manipulation. In some embodiments, agents capable of causing chemotaxis of endothelial progenitor cells can be administered in a localized manner to the area associated with lumbar hypoperfusion in order to accelerate recruitment of endothelial progenitors to anatomical regions that will be therapeutic for the treatment of lower back pain. Agents useful in this regard can include the various isoforms of the cytokine VEGF or SDF-1. Additionally, small molecule agonists of the VEGFR-1 and/or VEGFR2, and/or CXCR4 can be substituted instead of the mentioned chemotactic factors. Localization of said chemotactic factors to the area causative of the lumbar hypoperfusion can be performed using agents such as fibrin glue or certain delivery polymers known to one who is skilled in the art. These can include, for example: polyvinyl chloride, polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, polyethylene oxide, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl flouride, polyvinyl imidazole, chlorosulphonated polyolifins, and polyvinyl alcohol. Acceptable carriers, excipients, or stabilizers are also contemplated within the current invention, said carriers, exipients and stabilizers being relatively nontoxic to recipients at the dosages and concentrations employed, and can include buffers such as phosphate, citrate, and other organic acids; antioxidants including ascorbic acid, n-acetylcysteine, alpha tocopherol, and methionine; preservatives such as hexamethonium chloride; octadecyldimethylbenzyl ammonium chloride; benzalkonium chloride; phenol, benzyl alcohol, or butyl; alkyl parabens such as methyl or propyl paraben; catechol; resorcinol; cyclohexinol; 3-pentanol; and me-cresol); low molecular weight polypeptides; proteins, such as gelatin, or non-specific immunoglobulins; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose, or sorbitol; salt-forming counter-ions such as sodium; metal complexes.

In addition, the localization of chemoattractant factors to said area causative of lumbar hypoperfusion, can be used in conjunction with the systemic administration of natural suppressor and/or angiogenesis stimulating cells.

Administration of natural suppressor cells can be performed as a combination of said cells with other cell types useful for stimulation of angiogenesis. For example, whole bone marrow can be administered under the concept that the heterogeneous populations of cells found therein will contain not only anti-inflammatory natural suppressor cells, but also populations of cells capable of directly transforming into endothelial cells. In another embodiment, various cellular titrations and combinations can be used. For example, a standard "universal-donor" natural suppressor cell population can be generated and expanded for providing an anti-inflammatory effect, while the angiogenic stimulatory activity can be provided by the autologous bone marrow derived endothelial precursor cells.

In another aspect of the invention, cells capable of stimulating angiogenesis that concurrently possess anti-inflammatory activities are mesenchymal stem cells. As described above, mesenchymal stem cells can be derived in various quantities from bone marrow, umbilical cord blood, or adipose tissue. Accordingly, one aspect of the invention is the use of allogeneic umbilical cord blood cells for treatment of lower back pain through concurrently inhibiting inflammation and stimulation of angiogenesis. Cells can be matched with the recipient according to HLA typing within a continuum of haplotypes differences. For example, all 6 HLA loci can be matched or the cells can be completely mismatched. In practitioner of the invention will decide the degree of matching appropriate for each situation. In the literature it is reported that matching 4 out of six HLA loci in cord blood transplants is equivalent to matching 5 out of 6 in bone marrow transplants when assessing success rates and incidence of graft versus host disease (Chao, et al. 2004. *Hematology (Am Soc Hematol Educ Program)*:354-371, which is incorporated by reference herein in its entirety). It is to be noted that within the practice of the present invention, the desired result is not chimeric or donor hematopoiesis, but the duality of anti-inflammatory activity and stimulation of angiogenesis. Accordingly, doses and procedures used in the context of conventional cord blood transplants, whose aim is hematopoietic reconstitution, are not necessarily transferable to the aims of the invention disclosed. However cells associated with hematopoiesis can be useful in the context of the invention. Specific cells in cord blood associated with anti-inflammatory activity include CD4+ CD25+ Treg cells that are found in higher concentrations in cord blood as opposed to peripheral circulation (Takahata, et al. 2004. *Exp Hematol* 32:622-629, which is incorporated by reference herein in its entirety). In a study by Chang et al., it was demonstrated that cord blood CD4+ CD25+ Treg cells are potently inhibitory in allogeneic settings, expressing functional and phenotypic markers to conventional CD4+ CD25+ Treg cells found in adult peripheral circulation (Chang, et al. 2005. *Exp Hematol* 33:1508-1520, which is incorporated by reference herein in its entirety). The ability to expand cord blood CD4+ CD25+ Treg cells ex vivo (Kim, et al. 2005. *Tohoku J Exp Med* 205:115-122, which is incorporated by reference herein in its entirety), allows this invention to be practiced not only through direct administration of unseparated cord blood populations, but also to expand said CD4+ CD25+ Treg cells ex vivo, followed by local or systemic administration in the presence or absence of angiogenic cells in order to induce an anti-inflammatory effect in patients with lower back pain. Additional anti-inflammatory cells residing in the cord blood are natural killer T (NKT) cells (Liu, et al. 2006. *Zhongguo Shi Yan Xue Ye Xue Za Zhi* 14:128-132; Okada, et al. 2006. *Eur J Immunol* 36:236-244, each of which is incorporated by reference herein in its entirety), which have been demonstrated in a variety of settings to inhibit inflammatory autoimmune diseases such as experimental autoimmune encephalomyelitis and autoimmune type I diabetes (Sharif, et al. 2001. *Nat Med* 7:1057-1062; Kojo, et al. 2005. *J Immunol* 175:3648-3655, each of which is incorporated by reference herein in its entirety). These studies demonstrated that anti-inflammatory activities NKT cells are mediated through induction of "regulatory dendritic cells", as well as production and anti-inflammatory soluble mediators such as IL-4 and IL-10. Accordingly, another aspect of the invention disclosed teaches the use of cord blood derived, and/or ex vivo expanded, NKT cells for use in the stimulation of anti-inflammatory activity in patients with lower back pain, administered alone or together with angiogenesis stimulating cells.

The suitability of cord blood derived cells for use in the practice of the present invention is further supported by the fact that numerous patients to whom the invention is applicable to will not be able or willing to undergo the invasive process of bone marrow harvest. The use of allogeneic bone marrow is contemplated within the scope of the invention, however certain patients may not opt for this approach due to fear graft versus host disease development. The use of cord blood is therefore preferred for certain patients due to the known lower incidence of graft versus host disease when cord blood transplants are performed (Rubinstein, et al. 1998. *N Engl J Med* 339:1565-1577; Sirchia, et al. 1999. *Haematologica* 84:738-747, each of which is incorporated by reference herein in its entirety). Additionally, the same two studies cited also report lower level of viral contamination and increased availability of donors (due to laxer HLA-matching criteria) in patients receiving cord blood as opposed to bone marrow grafts.

In one particular embodiment, cord blood is collected from placenta of full-term deliveries in a multiple bag system containing citrate phosphate dextrose buffer or another suitable anti-coagulant and processed within 24 hours of collection. Anticoagulated cord blood is diluted 1:1 with 2 mM EDTA/PBS. Mononuclear cells are separated by gradient centrifugation as known in the art. For example, centrifugation can be performed at 450 g for 30 min at room temperature using Ficoll-Hypaque density gradient solution. Cells are seeded at a density of $1 \times 10^6$ cells/cm$^2$ into culture plates pre-coated with autologous serum. 12-20 hours after plating, the non-adherent cells are removed by washing the plate with phosphate buffered saline. Cells are passaged by trypsinization when confluence is reached and passaged as needed, approximately once every three days. Cells can be cultured in a wide variety of vessels such as bioreactors, flasks, plates, or other means. Culture medium useful for growing and expanding mesenchymal stem cells is widely known in the art and can include RMPI, DMEM, or MSCGM (Cambrex). When an appropriate number of cells is reached, cells are harvested and either cryopreserved for later use or administered intramuscularly into the lumbar area in proximity to the region of blood flow occlusion. Methods of administration and subsequent patient assessment are well-known in the art and briefly reviewed in this disclosure above.

Another embodiment involves the use of mesenchymal cells collected from either autologous or allogeneic adipose tissue. Collection of cells from this source is well described in the literature and is subject to several patent applications and issued patents. Similar to mesenchymal stem cells derived from other sources, adipose derived stem cells express markers such as CD9; CD29 (integrin beta 1); CD44 (hyaluronate receptor); CD49d,e (integrin alpha 4, 5); CD55 (decay accelerating factor); CD105 (endoglin); CD106 (VCAM-1); CD166 (ALCAM). These markers are useful not only for identification but can be used as a means of positive selection, before and/or after culture in order to increase purity of the desired cell population. In terms of purification and isolation, devices are known to those skilled in the art for rapid extraction and purification of cells adipose tissues. U.S. Pat. No. 6,316,247, which is incorporated by reference herein in its entirety, describes a device which purifies mononuclear adipose derived stem cells in an enclosed environment without the need for setting up a GMP/GTP cell processing laboratory so that patients can be treated in a wide variety of settings. One embodiment of the invention involves attaining 10-200 ml of raw lipoaspirate, washing said lipoaspirate in phosphate buffered saline, digesting said lipoaspirate with 0.075% collagenase type I for 30-60 min at 37° C. with gentle agitation, neutralizing said collagenase with DMEM or other medium containing autologous serum, preferably at a concentration of 10% v/v, centrifuging the treated lipoaspirate at approximately 700-2000 g for 5-15 minutes, followed by resuspension of said cells in an appropriate medium such as DMEM. Cells are subsequently filtered using a cell strainer, for example a 100 µm nylon cell strainer in order to remove debris. Filtered cells are subsequently centrifuged again at approximately 700-2000 g for 5-15 minutes and resuspended at a concentration of approximately $1 \times 10^6$/cm$^2$ into culture flasks or similar vessels. After 10-20 hours of culture non-adherent cells are removed by washing with PBS and remaining cells are cultured at similar conditions as described above for culture of cord blood derived mesenchymal stem cells. Upon reaching a concentration desired for clinical use, cells are harvested, assessed for purity and administered in a patient in need thereof as described above.

In another embodiment of the invention, cells suitable for treatment of lower back pain are purified from an allogeneic or autologous donor from peripheral blood through the use of stem cell mobilization. The mobilization allows a marked increase in the number of circulating stem cells and therefore allows for harvest of cells with desired properties for practice of the invention without the need to perform bone marrow puncture. A variety of methods to induce mobilization are known. Methods such as administration of cytotoxic chemotherapy, such as cyclophosphamide are effective but not preferred in the context of the current invention due to relatively unacceptable adverse events profile. Suitable agents useful for mobilization include but are not limited to: granulocyte colony stimulating factor (G-CSF), granulocyte-macrophage colony stimulating factor (GM-CSF), interleukin 1 (IL-1), interleukin 3 (IL-3), stem cell factor (SCF, also known as steel factor or kit ligand), vascular endothelial growth factor (VEGF), Flt-3 ligand, platelet-derived growth factor (PDGF), epidermal growth factor (EGF), fibroblast growth factor-1 (FGF-1), fibroblast growth factor-2 (FGF-2), thrombopoietin (TPO), interleukin-11 (IL-11), insulin-like growth factor-1 (IGF-1), megakaryocyte growth and development factor (MGDF), nerve growth factor (NGF), 3-hydroxy-3-methyl glutaryl coenzyme A (HMG CoA)reductase inhibitors, and the like.

In a preferred embodiment, donors are mobilized by administration of G-CSF (filgrastim: neupogen) at a concentration of 10 µg/kg/day by subcutaneous injection for 2-7 days, more preferably 4-5 days. Peripheral blood mononuclear cells are collected using an apheresis device such as the AS104 cell separator (Fresenius Medical). $1-4\times10^{10}$ mononuclear cells are collected, concentrated and injected into the area of lumbar blood flow occlusion in an intramuscular manner. Variations of this procedure can include steps such as subsequent culture of cells to enrich for various populations known to possess angiogenic and/or anti-inflammatory activities. Additionally cells can be purified for specific subtypes before and/or after culture. Treatments can be made to the cells during culture or at specific timepoints during ex vivo culture but before infusion in order to generate and/or expand specific subtypes and/or functional properties.

EXAMPLES

The following examples are offered to illustrate, but not to limit, the claimed invention. These examples are given to enable those of ordinary skill in the art to more clearly understand and to practice the present invention. The examples should not be considered as limiting the scope of the invention, but merely as be illustrative and representative thereof.

Example 1

Treatment of Lower Back Pain Through Localized Administration of Cord Blood Derived Stem Cells Patients between ages of 20 and 70 years old are randomly selected suffering from chronic lower back pain for the past 3 months that is unresponsive to conventional treatments such as physical therapy, nonsteroidal anti-inflammatory agents or other non-surgical available treatment options. At study baseline assessment patients present with an Owestry Disability Index for Back Pain score of 21-80% (From Moderate Disability to Crippling) and a pain measurement according to the Visual Analogue Score of >5. Patients are excluded if evidence, or suspicion of nerve root compression by disc prolapse/protrusion, spinal stenosis, infection, or tumors is present. Female subjects who are of child-bearing age and refuse to take contraceptives are also excluded, as well as patients with previous malignancies and ocular degenerative diseases including but not limited to macular degeneration.

Patients meeting this initial entrance criteria are subject to lumbar T2-weighted magnetic resonance analysis using midsagittal fast spin-echo (repetition time 4000-5000 milliseconds/echo time 120 milliseconds) images, performed by MRI scanner with a field strength of 1.5 Tesla (Siemens Magnetom Symphony, Siemens AG, Erlangen, Germany) as described (Kauppila et al. 2004, supra). Classification of lumbar intervertebral disc degeneration is performed using the method of Pfirrmann et al. (Pfirrmann, et al. 2001. *Spine* 26:1873-1878, which is incorporated by reference herein in its entirety). Briefly, if the nucleus pulposus is viewed as a homogenous white structure, without apparent abnormalities, a Grade I of disc degeneration is assigned. If the nucleus pulposus is observed as an inhomogenous white structure with possible horizontal bands across is, then a Grade II of disc degeneration is assigned. If a clear distinction is made between the nucleus pulposus and the annulus fibrosus, then a Grade III of disc degeneration is assigned. If the previous conditions are met but there is no collapse in disc space then the Grade IV is assigned, whereas if there is collapsed disc space then Grade V is assigned. Only patients presenting with Grade IV and V disc degeneration are included in the clinical study.

Subsequent to determination of disc degeneration grade, an assessment is made of blood flow in the areas associated with disc degeneration. Due to the fact that the abdominal aorta branches off into 4 lumbar arteries on each side of the spine, as well as the media sacral artery from the inferior of the aorta, assessment of these blood vessels is made using magnetic resonance aortography. Briefly, magnetic resonance imagining is conducting using a scanner with a field strength of 1.5 Tesla as previously described for the lumbar areas (Kauppila et al. 2004, supra), as well as similarly for kidneys (Boss, et al. 2006. *Eur Radiol.*, which is incorporated by reference herein in its entirety). Localization of the abdominal aorta is performed using a scout with a turboflash technique. The time interval for exact timing of the contrast enhanced three-dimensional angiography is determined with an initial injection of contrast media. The sequence, turboflash with a 10-mm-thick slice is taken, one slice per second, 40 slices at the level of the first lumbar vertebra and proceeding anteriorly. Intravenous injection of 2 mL Magnevist contrast medium followed by administration of saline is started simultaneously with the sequence. The peak T1 intensity of the test bolus is determined from a circular area in the aorta drawn by the computer. To obtain contrast-enhanced images a three-dimensional turboflash technique is used. Three measurements are taken. The initial one is performed in absence of contrast as a control for subtraction. The second and third images are made to correspond with the arterial and venous phases, and are taken in the presence of Magnevist injection, followed by saline injection at a rate of 2.5 mL/sec. The first measurement is subtracted from the second and third ones, and 12 sagittal maximum intensity projection images are made so as to cover 360° axially. The arteries are analyzed from these images by experts radiologist.

Thirty patients identified by this method as possessing a 50% or greater occlusion of one or more of the arteries supplying the lumbar circulatory system are permitted to enter receive treatment. The occluded lumbar artery is defined anatomically and is used to guide the physician during cell administration.

Umbilical cord blood is purified according to routine methods (Rubinstein, et al. 1995. *Proc Natl Acad Sci USA* 92:10119-10122, which is incorporated by reference herein in its entirety). Briefly, a 16-gauge needle from a standard Baxter 450-ml blood donor set containing CPD A anticoagulant (citrate/phosphate/dextrose/adenine) (Baxter Health Care, Deerfield, Ill.) is inserted and used to puncture the umbilical vein of a placenta obtained from healthy delivery from a mother tested for viral and bacterial infections according to international donor standards. Cord blood is allowed to drain by gravity so as to drip into the blood bag.

The placenta is placed in a plastic-lined, absorbent cotton pad suspended from a specially constructed support frame in order to allow collection and reduce the contamination with maternal blood and other secretions. The 63 ml of CPD A used in the standard blood transfusion bag, calculated for 450 ml of blood, is reduced to 23 ml by draining 40 ml into a graduated cylinder just prior to collection. This volume of anticoagulant matches better the cord volumes usually retrieved (<170 ml).

An aliquot of the blood is removed for safety testing according to the standards of the National Marrow Donor Program (NMDP) guidelines. Safety testing includes routine laboratory detection of human immunodeficiency virus 1 and 2, human T-cell lymphotropic virus I and II, Hepatitis B virus, Hepatitis C virus, Cytomegalovirus and Syphilis. Subsequently, 6% (wt/vol) hydroxyethyl starch is added to the anticoagulated cord blood to a final concentration of 1.2%: The leukocyte rich supernatant is then separated by centrifuging the cord blood hydroxyethyl starch mixture in the original collection blood bag (50×g for 5 min at 10° C.). The leukocyte-rich supernatant is expressed from the bag into a 150-ml Plasma Transfer bag (Baxter Health Care) and centrifuged (400×g for 10 min) to sediment the cells. Surplus supernatant plasma is transferred into a second Plasma Transfer bag without severing the connecting tube. Finally, the sedimented leukocytes are resuspended in supernatant plasma to a total volume of 20 ml. Approximately $5 \times 10^8$-$7 \times 10^9$ nucleated cells are obtained per cord. Cells are cryopreserved according to the method described by Rubinstein et al., Id., for subsequent cellular therapy.

Patients are HLA-matched to HLA-A and HLA-B using serotyping and to HLA-DR using genetic analysis. Patients are matched to the cord blood to 2 HLA-loci. Upon identification of suitable donor cord blood cells, cells are thawed, and assessed for viability and purity according to the method published by Rubinstein et al., Id., which is incorporated by reference herein in its entirety). Cells are washed and concentrated to a volume of 10 ml in UPS saline with 5% autologous serum. The total cell concentration of $1 \times 10^8$ cells per ml is obtained: total cell injection number is $5 \times 10^8$ per patient.

Based on the lumbar artery or medial sacral artery identified by MRI to be occluded, the area of injection is chosen. The surface area is cleaned with an iodine-based solution and covered with a sterile drape. Lidocaine (5 ml, 1% Abbott Laboratories, North Chicago, Ill.) is administered for local anesthesia according to standard medical practice. Ultrasound imaging is performed using either linear (5-13 MHz) or curved phased array (5-7 MHz) transducers, based on depth and local geometry needed to inject the psoas major muscle in proximity to area of occlusion. Needle selection is based on specific anatomic requirements as determined by the previous MRI, with 22- or 20-gauge spinal needles used in most of the patients. A freehand technique is used for administration with the patient in a supine position. A sonologist or radiologist positioned the transducer, and a radiologist positioned the needle and performed the injection procedure according to methods described for the injection of analgesics into the psoas major muscle (Sofka, et al. 2001. *J Ultrasound Med* 20:21-26; Adler, et al. 2005. *AJR Am J Roentgenol* 185:940-943, each of which is incorporated by reference herein in its entirety). The total injection volume of 5 ml is administered by gentle push (2-3 minutes in total) under ultrasound guidance. Ultrasonographic assessment of the increase in psoas muscle size is used to inform the injector that the appropriate injection site is injected.

Patients are subsequently observed for 3 hours for potential adverse effects from the injection procedure and are discharged. Patients are observed weekly for the first 4 weeks and subsequently monthly for an additional 5 months. Assessment of general health by physical exam and vital signs measurements is performed at each visit. Efficacy is determined by the Oswerty disability index, as well as the visual analogue pain score as routinely performed in clinical evaluation of lower back pain interventions. At the 3 months and 6 months after administration of cells, patients are performed an MRI artery analysis similarly to the one they underwent prior to administration of cell therapy. Additionally, at 6 months MRI disc assessment is performed and analyzed using the Grade I-IV system for disc degeneration described.

Of the 30 patients injected 27 observe improvement in both the Oswerty disability index and the visual analogue pain score beginning on week 2-post injection and maintained throughout the observation period of 6 months. Additionally, 24 of the patients report a self-directed decrease in analgesic intake due to reduction in overall pain. MRI artery analysis at 3 months indicates an increased "blushing" in 27 of the patients, in the area proximal to occluded vessels in comparison to the baseline assessment prior to cell therapy. Said blushing is indicative of neoangiogenesis. At the 6 month analysis the increased vascular presence as indicated by the blushing is maintained and in 7 patients is actually increased. MRI disc assessment at the 6 month period indicates reversion in disc degeneration in 17 patients by 1 grade according to the Pfirrmann score described above. In 5 patients the degree of degeneration is reversed by 2 grades.

No treatment associated serious adverse events are reported, although 3 patients complained of mild pain in proximity to the injection site.

Example 2

Treatment of Lower Back Pain Through Systemic Administration of Cord Blood Derived Stem Cells Thirty patients fitting the inclusion/exclusion criteria from EXAMPLE 1 are injected systemically with dose of $5 \times 10^7$ cord blood mononuclear cells isolated as described in the same example. Intravenous injection is performed over a period of 60 minutes with cells resuspended in USP saline and 5% autologous serum. Patients are subsequently observed for 3 hours for potential adverse effects from the administration of cell therapy and are discharged. Patients are observed weekly for the first 4 weeks and subsequently monthly for an additional 5 months. Assessment of general health by physical exam and vital signs measurements is performed at each visit. Efficacy is determined by the Oswerty disability index, as well as the visual analogue pain score as routinely performed in clinical evaluation of lower back pain interventions. Of the 30 patients injected 20 report improvement in both the Oswerty disability index and the visual analogue pain score beginning on week 2-post injection and maintained throughout the observation period of 6 months. An additional 8 patients report periodic improvement of Oswerty disability index and the visual analogue pain score followed by relapse to previous levels. Additionally, 18 of the patients report a self-directed decrease in analgesic intake due to reduction in overall pain.

Example 3

Treatment of Lower Back Pain Through Local Administration of Bone Marrow Derived Stem Cells Twenty patients fitting the inclusion/exclusion criteria from EXAMPLE 1 are assessed in a similar manner, including MRI artery and disc assessment. Patients are subjected to a bone marrow harvest. Briefly, patients are positioned face down on a horizontal platform and provided analgesics as per standard medical procedures. All personnel involved in the procedure are dressed in sterile surgical gowning and masks. The harvesting field comprising of both iliac crests is prepared by topically applying standard disinfectant solution. Iliac crests are anaesthetized and the harvesting needle is inserted in order to puncture the iliac crest. The cap and stylet of the harvesting needle is removed and 3-ml of marrow is harvested into the 15-ml harvesting syringe containing heparin solution. The process is repeated and the contents of the harvesting syringe are transferred into a 500-ml collecting bag. Approximately 75-125 ml of bone marrow is harvested in total.

Isolation of mononuclear cells is performed by gradient separation using the Hetastarch method, which is clinically applicable and reported to remove not only erythrocytes but also granulocytic cells. The previously published method of Montuoro et al is used (Montuoro, et al. 1991. *Haematologica* 76 Suppl 1:7-9, which is incorporated by reference herein in its entirety). Briefly, six-percent (wt/vol) Hetastarch (HES40, Hishiyama Pharmaceutical Co., Osaka, Japan) is added to the collected bone marrow sample to achieve a final concentration of 1.2 percent Hetastarch, (1:5 volume ratio of added Hetastarch to bone marrow). Centrifugation at 50 g for 5 min at 10° C. is performed in order to generate a leukocyte rich supernatant. Sedimentation of bone marrow takes place at a cell concentration of no more than $15 \times 10^6$ cells/ml in a total volume of 850 ml per Hetastarch bag. The supernatant is transferred into a plasma transfer bag and centrifuged (400 g for 10 min) to sediment the cells. The sedimented cells are subsequently washed in phosphate buffered saline in the presence of 5% penicillin/streptomycin mixture (Gibco, Mississauga, Canada) and 5% autologous serum. Cellular viability and lack of potential contamination with other cells is assessed by microscopy. Bone marrow mononuclear cells are subsequently concentrated in USP saline. The total cell concentration of $3 \times 10^8$ cells per ml is obtained: total cell injection number is $15 \times 10^8$ per patient in a volume of 5 ml. Injection procedure is performed according to description in EXAMPLE 1.

Of the 20 patients treated, 18 report improvement in both the Oswerty disability index and the visual analogue pain score beginning on week 2-post injection and maintained throughout the observation period of 6 months. Additionally, 15 of the patients report a self-directed decrease in analgesic intake due to reduction in overall pain. Two patients report an increased appetite starting after 2 and 4 weeks subsequent to cell therapy administration.

MRI artery analysis at 3 months indicates an increased "blushing" in the area proximal to occluded vessels in comparison to the baseline assessment prior to cell therapy in 17 of the patients treated. At the 6 month analysis the increased vascular presence as indicated by the blushing is maintained and in 4 patients is actually increased. MRI disc assessment at the 6 month period indicates reversion in disc degeneration in 15 patients by 1 grade according to the Pfirrmann score described above. In 3 patients the degree of degeneration is reversed by 2 grades.

Safety assessments include: presence of calcification by imaging the area of cellular administration, physical and medical abnormalities, and alterations in enzymes and hematological parameters. Safety assessments are performed at each visit following administration of cellular therapy. No treatment-associated alterations in safety parameters assessed are observed. Furthermore, no treatment associated serious adverse events are reported, although 3 patients complained of mild pain in proximity to the injection site.

Example 4

Treatment of Lower Back Pain Through Local Administration of Umbilical Cord Blood Derived Mesenchymal Stem Cells Thirty patients fitting the inclusion/exclusion criteria from EXAMPLE 1 are assessed in a similar manner, including MRI artery and disc assessment. Cord blood is obtained, processed and HLA-matched according to EXAMPLE 2. Cord blood mononuclear cells are seeded at a density of $1 \times 10^6$ cells/cm$^2$ into culture flasks in a Good Manufacturing Procedures-compliant sterile clean room. Cells are cultured in DMEM-LG media (Life Technologies), supplemented with 10% autologous serum. On day 4, nonadherent cells are discarded and fresh tissue culture medium is added. On day 7, cultures are tested for sterility, nonadherent cells are discarded by washing culture flasks with USP saline containing 10% autologous serum, and the remaining adherent cells are washed with Tyrode's Salt Solution (Sigma, St. Louis, Mo.) and incubated for 1 hr in M199 mediua (Life Technologies). Cells are detached with 0.05% trypsin-EDTA (Life Technologies), and are resuspended in M199 supplemented with 10% of autologous serum. Cells are subcultured for an 12 days with feeding of cultures performed every 3 days. The cells are subsequently harvested by trypsinization as described above, counted and an aliquot is taken for flow cytometric analyzes for the expression of mesenchymal stem cells markers and lack of expression of hematopoietic markers. Cell batches of >95% purity for CD73, and CD105, and less than 5% contamination of CD45 expressing cells are chosen for cell therapy.

Cells are implanted into patients as described in EXAMPLE 1, with exception to concentration. Cell concentration is adjusted to $5 \times 10^6$ cells per ml in USP saline supplemented with 10% autologous serum and injected in a volume of 5 ml.

Of the 30 patients treated, 29 report improvement in both the Oswerty disability index and the visual analogue pain score beginning on week 2-post injection and the response is maintained throughout the observation period of 6 months. Additionally, 23 of the patients report a self-directed decrease in analgesic intake due to reduction in overall pain.

MRI artery analysis at 3 months indicates an increased "blushing" in the area proximal to occluded vessels in comparison to the baseline assessment prior to cell therapy in 25 of the patients treated. At the 6 month analysis the increased vascular presence as indicated by the blushing is maintained and in 11 patients is actually increased. MRI disc assessment at the 6 month period indicates reversion in disc degeneration in 23 patients by 1 grade according to the Pfirrmann score described above. In 7 patients the degree of degeneration is reversed by 2 grades.

Importantly, no adverse effects are observed related to treatment. Analysis of potential calcification and ectopic bone formation is performed in all treated patients due to the possible ability of mesenchymal cells to differentiate into a variety of mesodermal lineage. Neither calcification or ectopic bone neogenesis are observed by x-ray analysis.

Example 5

Treatment of Lower Back Pain Through Local Administration of Umbilical Cord Blood Derived Mesenchymal Stem Cells and Systemic Anti-Inflammatory CD4+ CD25+ cells Thirty patients are selected based on the criteria of EXAMPLE 1. Cellular purification procedures and administration, as well as patient observation and follow-up are performed as described in EXAMPLE 4, with the exception that apheresis is performed using a Fresenius AS 104 Cell Separator to isolate approximately $10 \times 10^8$ mononuclear cells from peripheral blood. Lymphocytes are purified by gradient centrifugation and selection of CD4+ CD25+ T cells is performed using the Clini-MACs system according to the manufacturer's instructions.

A total yield of approximately $5 \times 10^6$ CD4+ CD25+ cells are isolated per patient. Said cells are cultured in a GMP environment in AIM-V media supplemented with 5% autologous serum and stimulated with IL-2 at 100 Units/ml, together with TGF-beta 1-ng/ml and plate-bound anti-CD3 monoclonal antibody for a period of 3 days. Subsequently, cells are harvested, washed, assessed for viability and T cell suppressor activity and infused intravenously in all patients 24 hours prior to administration of mesenchymal stem cell therapy as described in EXAMPLE 4. Cell batches containing <95% viability are excluded from use, as well as cells not demonstrating >50% inhibitory activity to proliferation of autologous CD4+ CD25− cells stimulated with anti-CD3 and anti-CD28.

Subsequent to intravenous infusion of CD4+ CD25+ cells patients are observed for immediate reactions and remain under observation for the 24 hours until infusion of mesenchymal stem cell therapy is performed.

Of the 30 patients treated, 28 report improvement in both the Oswerty disability index and the visual analogue pain score beginning on week 2-post injection and the response is maintained throughout the observation period of 6 months. Additionally, 27 of the patients report a self-directed decrease in analgesic intake due to reduction in overall pain.

MRI artery analysis at 3 months indicates an increased "blushing" in the area proximal to occluded vessels in comparison to the baseline assessment prior to cell therapy in 26 of the patients treated. At the 6 month analysis the increased vascular presence as indicated by the blushing is maintained and in 21 patients is actually increased. MRI disc assessment at the 6 month period indicates reversion in disc degeneration in 25 patients by 1 grade according to the Pfirrmann score described above. In 12 patients the degree of degeneration is reversed by 2 grades.

Importantly, no adverse effects are observed related to the administration of combined angiogenesis stimulating cells and autologous activated CD4+ CD25+ anti-inflammatory T cells. No increase in infections, opportunistic diseases, or general immunosuppression is observed.

Example 6

Treatment of Lower Back Pain Through Local Administration of Umbilical Cord Blood Derived Mesenchymal Stem Cells and Systemic Anti-Inflammatory Myeloid Suppressor Cells Thirty patients are recruited according to the description in EXAMPLE 1. Said patients are subject to identical treatments and observations with the exception that autologous myeloid suppressor cells are used as part of the treatment.

Fourteen days prior to the scheduled date of cord blood cell infusion, bone marrow cells are harvested from patients as described in EXAMPLE 3. The total cell concentration of $3 \times 10^8$ cells per ml is obtained: total cell collection provides approximately $15 \times 10^8$ per patient. Cells are cultured in Teflon culture flasks in IMEM media supplemented with 10% autologous serum supplemented with 100 ng/ml of GM-CSF. Cells are fed 4 times in GMP conditions. Subsequent to a 12-day culture cells are isolated by percoll density gradient between 1.055-1.065 g/ml. Typical cell yield in comparison to starting population is approximately 10%. This is due to the known small percentage of low density myeloid cells found in the bone marrow naturally. Cell viability is assessed and only batches with >95% viability are released for use. Additionally, aliquots of cells are taken during the culture period and tested for ability to suppress an on-going mixed lymphocyte reaction between 2 HLA-mismatched, patient unrelated donor. Only batches of cells with inhibitor activity of >50% in a standard one suppressor cell to one stimulator cell to one responder cell as determined by tritiated thymidine intake are allowed to proceed to clinical use.

Two days prior to umbilical cord blood derived mesenchymal stem cell infusion, myeloid suppressor cells are infused intravenously in patients at a total concentration of $1 \times 10^8$ cells per patient.

Of the 30 patients treated, 28 report improvement in both the Oswerty disability index and the visual analogue pain score beginning on week 1-post injection and the response is maintained throughout the observation period of 6 months. Additionally, 23 of the patients report a self-directed decrease in analgesic intake due to reduction in overall pain.

MRI artery analysis at 3 months indicates an increased "blushing" in the area proximal to occluded vessels in comparison to the baseline assessment prior to cell therapy in 24 of the patients treated. At the 6 month analysis the increased vascular presence as indicated by the blushing is maintained and in 23 patients is actually increased MRI disc assessment at the 6 month period indicates reversion in disc degeneration in 29 patients by 1 grade according to the Pfirrmann score described above. In 1 patient the degree of degeneration is reversed by 2 grades.

No adverse events are reported related to the experimental intervention.

Example 7

Treatment of Lower Back Pain Through Systemic Administration of Anti-Inflammatory Natural Killer T Cells Thirty patients are recruited according to the description in EXAMPLE 1. Said patients are subject to identical observations with the exception that autologous NKT cells are are used as part of the treatment.

G-CSF is administered subcutaneously at a dosage of 300 µg/m$^2$ twice daily for 3 days prior to apheresis. On the day of apheresis, another dose of G-CSF is administered. Apheresis is performed as described in EXAMPLE 5.

Mononuclear cells are purified by centrifugation on Ficoll density gradient under GMP, cells are washed and subsequently cultured in culture flasks at 2.0×10$^5$ cells/mL in medium supplemented with 100 ng/mL alpha-galactosyl ceramide, 100 U/mL IL-2, and 100 ng/ml TGF-beta. Cells are cultured under standard conditions in AIM-V supplemented with 10% autologous serum as described (Harada, et al. 2005. *J Immunother* 28:314-321, which is incorporated by reference herein in its entirety).

After 12 days of culture, with 3 changes of media, Vα24$^+$ NKT cells are purified using the Clini-MACS system according to the manufacturer's instructions. A total of 5×10$^7$ cells are obtained on average. Said cells are subsequently washed, tested for viability, and subsequently used for therapy.

An average of 3×10$^7$ cells are injected intravenously in patients after reconstitution in USP saline containing 10% autologous serum. Patients are observed overnight and subsequently released.

Of the 30 patients treated, 24 report improvement in both the Oswerty disability index and the visual analogue pain score beginning on week 2-post injection and the response is maintained throughout the observation period of 6 months. Additionally, 10 of the patients report a self-directed decrease in analgesic intake due to reduction in overall pain.

MRI artery analysis at 3 months indicates no alterations in the occluded vessels in comparison to the baseline assessment prior to cell therapy. At the 6 month analysis there is appearance of increased blushing in 3 patients but results are significant in comparison to baseline values. MRI disc assessment at the 6-month period indicates no alteration in disc degeneration in the patients tested.

Of note, MRI analysis indicates complete resorption of herniated disc granulation tissue in 4 of 4 patients who presented with this as the cause of back pain.

What is claimed is:

1. A method of inhibition of disc degeneration in a patient, said method comprising:
   (a) identifying a patient having disc degenerative disease and in need of increased perfusion to the lumbar area; and
   (b) injecting about 5×10$^6$ to about 40×10$^9$ mesenchymal stem cells (MSC) directly into a lumbar associated muscle proximal to a lumbar disc of said patient, wherein the cells are autologous or allogeneic non-transfected MSC expressing cellular marker CD73 and CD105; wherein the lumbar associated muscle is selected from the group consisting of psoas major muscle, multifidus muscle, transversospinalis muscle and sacrospinalis muscle, and wherein the mesenchymal stem cells augment the rate of perfusion to the area of disc degeneration without causing calcification at the administration site.

2. The method of claim 1, wherein said cells are further identified by detecting the expression of one or more antigens selected from the group consisting of: STRO-1, CD105, CD54, CD106, HLA-I markers, vimentin, alpha-smooth muscle actin (ASMA), collagen-1 and fibronectin.

3. The method of claim 1, wherein said cells are injected directly into the psoas major muscle.

4. The method of claim 1, wherein said cells are injected under ultrasound guidance.

\* \* \* \* \*